US009322031B2

(12) United States Patent
Andersen et al.

(10) Patent No.: US 9,322,031 B2
(45) Date of Patent: Apr. 26, 2016

(54) TRANSGENIC PLANTS WITH ENHANCED AGRONOMIC TRAITS

(75) Inventors: Scott E. Andersen, St. Louis, MO (US); Yongwei Cao, Chesterfield, MO (US); Stanton B. Dotson, Chesterfield, MO (US); Michael D. Edgerton, St. Louis, MO (US); David K. Kovalic, Clayton, MO (US); Linda L. Lutfiyya, St. Louis, MO (US); Zhidong Xie, Maryland Heights, MO (US); Gregory R. Heck, Crystal Lake Park, MO (US); Thomas J. La Rosa, Fenton, MO (US); Jingdong Liu, Chesterfield, MO (US); Jingrui Wu, Chesterfield, MO (US); Garrett J. Lee, Wayne, NJ (US); Thomas R. Adams, North Stonington, CT (US); Donald E. Nelson, Stonington, CT (US); Timothy Conner, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 129 days.

(21) Appl. No.: 13/444,802

(22) Filed: Apr. 11, 2012

(65) Prior Publication Data

US 2012/0317677 A1 Dec. 13, 2012

Related U.S. Application Data

(63) Continuation of application No. 11/982,010, filed on Oct. 31, 2007, now abandoned, which is a continuation-in-part of application No. 10/678,588, filed on Oct. 2, 2003, now abandoned.

(60) Provisional application No. 60/415,758, filed on Oct. 2, 2002, provisional application No. 60/425,157, filed on Nov. 8, 2002, provisional application No. 60/463,787, filed on Apr. 18, 2003.

(51) Int. Cl.
*C12N 15/82* (2006.01)
*A01H 1/06* (2006.01)

(52) U.S. Cl.
CPC .............. *C12N 15/8271* (2013.01); *A01H 1/06* (2013.01); *C12N 15/8273* (2013.01)

(58) Field of Classification Search
None
See application file for complete search history.

(56) References Cited

U.S. PATENT DOCUMENTS

| 5,322,938 A | 6/1994 | McPherson et al. |
|---|---|---|
| 5,641,876 A | 6/1997 | McElroy et al. |
| 6,084,089 A | 7/2000 | Mine et al. |
| 6,140,078 A | 10/2000 | Sanders et al. |
| 6,162,965 A * | 12/2000 | Hansen ........................ 800/278 |
| 6,194,636 B1 | 2/2001 | McElroy et al. |
| 6,232,526 B1 | 5/2001 | McElroy et al. |
| 6,235,975 B1 * | 5/2001 | Harada et al. ................. 800/306 |
| 6,677,504 B2 | 1/2004 | Silva et al. |
| 6,717,034 B2 | 4/2004 | Jiang |
| 7,151,204 B2 | 12/2006 | Houmard et al. |
| 7,253,000 B2 | 8/2007 | Sivasankar et al. |
| 7,294,759 B2 | 11/2007 | Allen et al. |
| 7,317,141 B2 | 1/2008 | Sivasankar et al. |
| 7,345,217 B2 | 3/2008 | Zhang et al. |
| 7,482,511 B2 | 1/2009 | da Costa e Silva et al. |
| 7,511,130 B2 | 3/2009 | Heck et al. |
| 7,511,190 B2 | 3/2009 | Creelman et al. |
| 7,786,353 B2 | 8/2010 | Fernandes |
| 7,868,149 B2 | 1/2011 | Boukharov et al. |
| 7,868,229 B2 | 1/2011 | Ratcliffe et al. |
| 7,956,242 B2 | 6/2011 | Zhang et al. |
| 7,960,612 B2 | 6/2011 | Zhang et al. |
| 8,030,546 B2 | 10/2011 | Reuber et al. |
| 8,558,059 B2 | 10/2013 | Heard |
| 8,633,353 B2 | 1/2014 | Ratcliffe et al. |
| 2002/0102695 A1 | 8/2002 | Silva et al. |
| 2003/0093837 A1 | 5/2003 | Keddie et al. |
| 2003/0126638 A1 | 7/2003 | Allen et al. |
| 2003/0204870 A1 | 10/2003 | Allen et al. |
| 2003/0233670 A1 | 12/2003 | Edgerton et al. |
| 2004/0019927 A1 * | 1/2004 | Sherman et al. ............... 800/278 |
| 2004/0031072 A1 | 2/2004 | La Rosa et al. |
| 2004/0034888 A1 | 2/2004 | Liu et al. |

(Continued)

FOREIGN PATENT DOCUMENTS

| EP | 1230345 B1 | 6/2008 |
|---|---|---|
| WO | WO 02/057439 * | 7/2002 |

(Continued)

OTHER PUBLICATIONS

Nelson et al. (PNAS, 104:16450-16455, Published Oct. 16, 2007.*
Lotan et al. (Cell, 93:1195-1205, 1998).*
Li et al. (NCBI, GenBank Sequence Accession No. X59714, pp. 1-2, Published Nov. 15, 1992.*
Allen et al. (Crop evapotranspiration—Guidelines for computing crop water requirements—FAO Irrigation and drainage paper 56, FAO, 1998).*

(Continued)

*Primary Examiner* — Vinod Kumar
(74) *Attorney, Agent, or Firm* — Thompson Coburn LLP; Charles P. Romano

(57) ABSTRACT

This invention provides transgenic plant cells with recombinant DNA for expression of proteins that are useful for imparting enhanced agronomic trait(s) to transgenic crop plants. This invention also provides transgenic plants and progeny seed comprising the transgenic plant cells where the plants are selected for having an enhanced trait selected from the group of traits consisting of enhanced water use efficiency, enhanced cold tolerance, increased yield, enhanced nitrogen use efficiency, enhanced seed protein and enhanced seed oil. Also disclosed are methods for manufacturing transgenic seed and plants with enhanced traits.

9 Claims, 3 Drawing Sheets

(56) References Cited

U.S. PATENT DOCUMENTS

| | | | |
|---|---|---|---|
| 2004/0123347 A1 | 6/2004 | Hinchey et al. | |
| 2005/0022266 A1 | 1/2005 | Wu et al. | |
| 2005/0048556 A1 | 3/2005 | Heck et al. | |
| 2005/0086718 A1 | 4/2005 | Heard et al. | |
| 2005/0097640 A1 | 5/2005 | Fernandes | |
| 2005/0172364 A1 | 8/2005 | Heard | |
| 2006/0021087 A1 | 1/2006 | Baum et al. | |
| 2006/0242738 A1 | 10/2006 | Sherman et al. | |
| 2007/0039076 A1 | 2/2007 | Boukharov et al. | |
| 2007/0192889 A1 | 8/2007 | La Rosa et al. | |
| 2007/0199107 A1* | 8/2007 | Ratcliffe et al. | 800/287 |
| 2008/0040973 A1 | 2/2008 | Nelson et al. | |
| 2008/0104730 A1 | 5/2008 | Wu et al. | |
| 2008/0163397 A1* | 7/2008 | Ratcliffe et al. | 800/298 |
| 2008/0313756 A1* | 12/2008 | Zhang et al. | 800/260 |
| 2009/0044297 A1 | 2/2009 | Andersen et al. | |
| 2009/0049566 A1* | 2/2009 | Zhang et al. | 800/266 |
| 2009/0049573 A1 | 2/2009 | Dotson et al. | |
| 2009/0093620 A1 | 4/2009 | Kovalic et al. | |
| 2009/0100544 A1 | 4/2009 | Anstrom et al. | |
| 2009/0138981 A1* | 5/2009 | Repetti et al. | 800/263 |
| 2009/0183270 A1 | 7/2009 | Adams et al. | |
| 2009/0217414 A1* | 8/2009 | La Rosa et al. | 800/278 |
| 2009/0241217 A9* | 9/2009 | Wu et al. | 800/278 |
| 2010/0293663 A2 | 11/2010 | LaRosa et al. | |
| 2012/0022713 A1 | 1/2012 | Deaver, Sr. et al. | |
| 2012/0317677 A1 | 12/2012 | Andersen et al. | |

FOREIGN PATENT DOCUMENTS

| | | |
|---|---|---|
| WO | WO 02/057439 A2 | 7/2002 |
| WO | WO 03/008540 A2 | 1/2003 |
| WO | WO 2004/076638 A2 | 9/2004 |
| WO | 2005033318 A2 | 4/2005 |
| WO | WO 2005/033319 A2 | 4/2005 |
| WO | 2007028165 A2 | 3/2007 |
| WO | 2008002480 A2 | 1/2008 |
| WO | 2009049110 | 4/2009 |

OTHER PUBLICATIONS

U.S. Appl. No. 60/415,758, filed Oct. 2, 2002, Abad et al.
U.S. Appl. No. 60/425,157, filed Nov. 8, 2002, Wu et al.
Bork et al. "Go hunting in sequence databases but watch out for the traps," *TIG*, 12:425-427, 1996.
Doerks et al. "Protein annotation: detective work for function prediction," *TIG*, 14:248-250, 1998.
Edwards et al., "Multiple genes encoding the conserved CCAAT-box transcription factor complex are expressed in Arabidopsis," *Plant Physiology*, 117:1015-1022, 1998.
GenBank Sequence Accession No. X59714, dated Nov. 15, 1992.
Gordon et al., "RNAi for insect-proof plants," *Nature Biotechnology*, 25(11):1231-1232, 2007.
Guo et al., "Protein tolerance to random amino acid change," *PNAS*, 101:9205-9210, 2004.
Keskin et al., "A new, structurally nonredundant, diverse data set of protein—protein interfaces and its implications," *Protein Science*, 13:1043-1055, 2004.
Lee et al., "Arabidopsis Leafy COTYLEDON1 represents a functionally specialized subunit of the CCAAT binding transcription factor," *PNAS*, 100(4):2152-2156, 2003.
Li, et al., "Evolutionary variation of the CCAAT-binding transcription factor NF-Y," *Nucleic Acids Research*, 20(5):1087-1091, 1992.
Lotan et al., "Arabidopsis Leafy COTYLEDON1 is Sufficient to Induce Embryo Development in Vegetative Cells," *Cell*, 93(7):1195-1205, 1998.
Mantovani R., "The molecular biology of the CCAAT-binding factor NF-Y," *Gene*, 18;239(1):15-27, 1999.
Miyoshi et al., "OsHAP3 genes regulate chloroplast biogenesis in rice," *The Plant Journal*, 36(4):532-540, 2003.
Nelson et al., "Plant nuclear factor Y (NF-Y) B subunits confer drought tolerance and lead to improved corn yields on water-limited acres," *PNAS*, 104(42):16450-16455, 2007.
Ngo et al., "Computational complexity, protein structure prediction, and the levinthal paradox" in "The protein folding problem and tertiary structure prediction," K. Merz., and S. Le Grand (eds.), pp. 1-80, 1994.
Smith et al. "The challenges of genome sequence annotation or The devil is in the details," *Nature Biotechnology*, 15:1222-1223, 1997.
Stephenson et al., "Genome-wide identification and expression analysis of the NF-Y family of transcription factors in Triticum aestivum," *Plant Molecular Biology*, 65:77-92, 2007.
Thornton et al. "From structure to function: approaches and limitations," *Nature Structural Biology*, structural genomic supplement, 2000.
Vilardell et al., "Regulation of the maize rab17 gene promoter in transgenic heterologous systems," *Plant Molecular Biology*, 17:985-993, 1991.
Wells, "Additivity of mutational effects in proteins," *Biochemistry*, 29:8509-8517, 1990.
Xiao-Yan Li, *Nucleic Acids Research*, vol. 20, pp. 1087-1091, 1992.
Information Disclosure Statement for U.S. Appl. No. 10/678,588, filed Jun. 1, 2004.
Sequence alignment between the sequence encoded by SEQ ID No:29 in U.S. Appl. No. 11/821,176 vs. SEQ ID No:1764 in U.S. Appl. No. 11/982,010, dated May 17, 2010.
Sequence alignment between the sequence encoded by SEQ ID No. 30 in U.S. Appl. No. 11/821,176 vs. SEQ ID No. 1764 in U.S. Appl. No. 11/982,010, dated May 17, 2010.
Sequence alignment between the sequence encoded by SEQ ID No. 31 in U.S. Appl. No. 11/821,176 vs. SEQ ID No. 1764 in U.S. Appl. No. 11/982,010, dated May 17, 2010.
Sequence alignment between the sequence encoded by SEQ ID No. 32 in U.S. Appl. No. 11/821,176 vs. SEQ ID No. 1764 in U.S. Appl. No. 11/982,010, dated May 17, 2010.
Sequence alignment between the sequence encoded by SEQ ID No. 29 in U.S. Appl. No. 11/821,176 vs. SEQ ID No. 1765 in U.S. Appl. No. 11/982,274, dated May 12, 2010.
Sequence alignment between the sequence encoded by SEQ ID No. 30 in U.S. Appl. No. 11/821,176 vs. SEQ ID No. 1765 in U.S. Appl. No. 11/982,274, dated May 12, 2010.
Sequence alignment between the sequence encoded by SEQ ID No. 31 in U.S. Appl. No. 11/821,176 vs. SEQ ID No. 1765 in U.S. Appl. No. 11/982,274, dated May 12, 2010.
Sequence alignment between the sequence encoded by SEQ ID No. 32 in U.S. Appl. No. 11/821,176 vs. SEQ ID No. 1765 in U.S. Appl. No. 11/982,274, dated May 12, 2010.
Sequence alignment between the sequence encoded by SEQ ID No. 29 in U.S. Appl. No. 11/821,176 vs. SEQ ID No. 617 in U.S. Appl. No. 11/982,680, dated May 17, 2010.
Sequence alignment between the sequence encoded by SEQ ID No. 30 in U.S. Appl. No. 11/821,176 vs. SEQ ID No. 617 in U.S. Appl. No. 11/982,680, dated May 17, 2010.
Sequence alignment between the sequence encoded by SEQ ID No. 31 in U.S. Appl. No. 11/821,176 vs. SEQ ID No. 617 in U.S. Appl. No. 11/982,680, dated May 17, 2010.
Sequence alignment between the sequence encoded by SEQ ID No. 32 in U.S. Appl. No. 11/821,176 vs. SEQ ID No. 617 in U.S. Appl. No. 11/982,680, dated May 17, 2010.
Office Action regarding U.S. Appl. No. 11/982,274, dated Oct. 27, 2010.
Office Action Regarding U.S. Appl. No. 11/982,010, dated Jan. 6, 2011.
Office Action regarding U.S. Appl. No. 11/982,274, dated Jan. 6, 2011.
Office Action Regarding U.S. Appl. No. 11/982,680, dated Mar. 11, 2011.
Response to Office Action regarding U.S. Appl. No. 11/982,274, dated Apr. 27, 2011.
Information Disclosure Statement regarding U.S. Appl. No. 11/982,274, dated Apr. 27, 2011.
Supplemental Information Disclosure Statement for U.S. Appl. No. 11/982,010, filed Jun. 3, 2011.
Supplemental Information Disclosure Statement for U.S. Appl. No. 11/982,680, filed Jun. 3, 2011.

(56) References Cited

OTHER PUBLICATIONS

Amendment and Response to Office Action regarding U.S. Appl. No. 11/982,010, dated Jul. 6, 2011.
Final Office Action regarding U.S. Appl. No. 11/982,274, dated Aug. 1, 2011.
Notice of Abandonment regarding U.S. Appl. No. 11/982,680, dated Sep. 19, 2011.
Final Office Action regarding U.S. Appl. No. 11/982,010, dated Oct. 11, 2011.
Response to Final Office Action regarding U.S. Appl. No. 11/982,274, dated Feb. 1, 2012.
Notice of Abandonment regarding U.S. Appl. No. 11/982,010, dated Apr. 17, 2012.
Summary of drought tolerance data for NF-YB variants, undated (referenced in IDS for U.S. Appl. Nos. 11/982,274 and 11/982,680).
Summary of SEQ ID No. 29 data for yield under stress (SEQ ID No. 29 is NFYB2-S83A modified NF-YB2 protein of U.S. Appl. No. 11/821,176), undated.
Information Disclosure Statement filed for U.S. Appl. No. 13/444,802 on Sep. 12, 2012.
Anderson, John R., et al., "Managing Drought—Drought Advisory for Corn Production", Crop Strategies, North Carolina Cooperative Extension Service, AG 519-13, 1995, 6 pages.
Cai et al., "A Putative CCAAT-Binding Transcription Factor is a Regulator of Flowering Timing in Arabidopsis", Plant Physiology, Sep. 2007, pp. 98-105, vol. 145.
Cassel, E. Kim, et al., Aflatoxins: Hazards in Grain/Aflatoxicosis and Livestock, South Dakota State University Cooperative Extension Service, Oct. 2001, 4 pages, FS907.
Chen et al, "AtHAP3b Plays a Crucial Role in the Regulation of Flowering Time in Arabidopsis During Osmotic Stress", Journal of Biochemistry and Molecular Biology, Nov. 2007, pp. 1083-1089, vol. 40, No. 6.
Combier et al., "MtHAP2-1 is a Key Transcriptional Regulator of Symbiotic Nodule Development Regulated by microRNA169 in Medicago Truncatula", Genes and Development, 2006, pp. 3084-3088, vol. 20, Cold Spring Harbor Laboratory Press.
Diener, Urban L., et al., Epidemiology of Aflatoxin Formation by Aspergillus Flavus, Annual Review of Phytopathology, 1987, pp. 249-270, vol. 25.
Kumimoto et al., "The Nuclear Factor Y Subunits NF-YB2 and NF-YB3 Play Additive Roles in the Promotion of Flowering by Inductive Long-Day Photoperiods in Arabidopsis", Planta, 2008, pp. 709-723, vol. 228, Springer-Verlag.
Meinke et al., "Leafy Cotyledon Mutants of Arabidopsis", The Plant Cell, Aug. 1994, pp. 1049-1064, vol. 6.
Mette et. al., (EMBO J. 19:5194-51201, 2000).
Monsanto Modified NFYB Performance Summary, Apr. 12, 2010, 1 page.
Monsanto SEQ ID No. 29 Drought Tolerance Data, Apr. 12, 2010, 6 pages.
Mu et al., "Leafy Cotyledon1 is a Key Regulator of Fatty Acid Biosynthesis in Arabidopsis", Plant Physiology, Oct. 2008, pp. 1042-1054, vol. 148.
Xu, Wenwei, et al., Progress Toward Developing Stress-Tolerant and Low-Aflatoxin Corn Hybrids for the Southern States [abstract], 16th Annual Aflatoxin Elimination Workshop Proceedings, Oct. 3, 2003, p. 63. Obtained from United States Department of Agriculture Agricultural Research Service, http://www.ars.usda.gov, 2 pages.
Yamamoto et al., "Arabidopsis NF-YB Subunits LEC1 and LEC1-Like Activate Transcription by Interacting with Seed-Specific Abre-Binding Factors", The Plant Journal, 2009, pp. 843-856, vol. 58, Blackwell Publishing Ltd.
Zanetti et al., "A C Subunit of the Plant Nuclear Factor NF-Y Required for Rhizobial Infection and Nodule Development Affects Partner Selection in the Common Bean-Rhizobium etli Symbiosis", The Plant Cell, Dec. 2010, pp. 4142-4157, vol. 22.
Ingram et al., "The Molecular Basis of Dehydration Tolerance in Plants", Annual Review of Plant Physiology and Plant Molecular Biology, Jun. 1996, pp. 377-403, vol. 47.
Urao et al., "A Transcriptional Activation Domain of ATMYb2, a Drought-Inducible Arabidopsis Myb-Related Protein", The Plant Journal, Dec. 1996, pp. 1145-1148, vol. 10 Issue 6.
Shinozaki et al., "Gene Expression and Signal Transduction in Water-Stress Response", Plant Physiology, Oct. 1997, pp. 327-334, vol. 115 Issue 2.
Liu et al., "Two Transcription Factors, DREB1 and DREB2, with an EREBP/AP2 DNA Binding Domain Separate Two Cellular Signal Transduction Pathways in Drought- and Low-Temperature-Responsive Gene Expression, Respectively, in Arabidopsis", The Plant Cell, Aug. 1998, pp. 1391-1406, vol. 10 Issue 8.
Jaglo-Ottosen et al., "Arabidopsis CBF1 Overexpression Induces COR Genes and Enhances Freezing Tolerance", Science, Apr. 3, 1998, pp. 104-106, vol. 280 No. 5360.
Gilmour et al., "Low Temperature Regulation of the Arabidopsis CBF Family of AP2 Transcriptional Activators as an Early Step in Cold-Induced COR Gene Expression", The Plant Journal, Nov. 1998, pp. 433-442, vol. 16 Issue 4.

* cited by examiner

Fig 1. Plasmid map of pMON93039
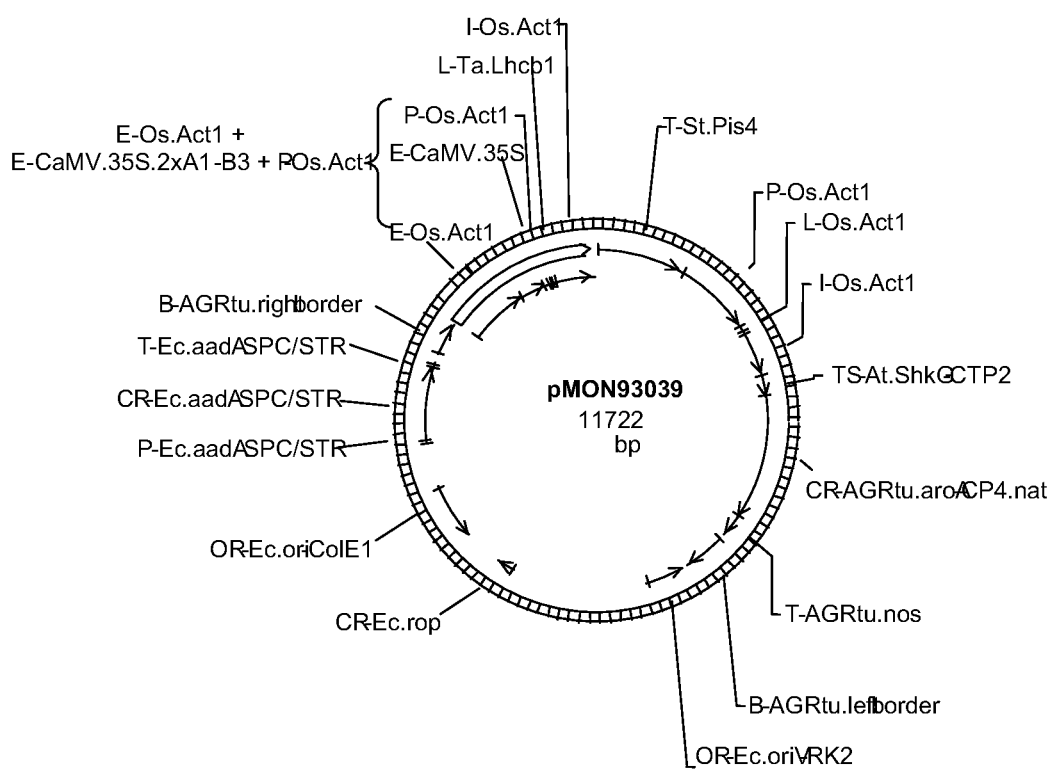

FIG. 2 Plasmid map of pMON82053
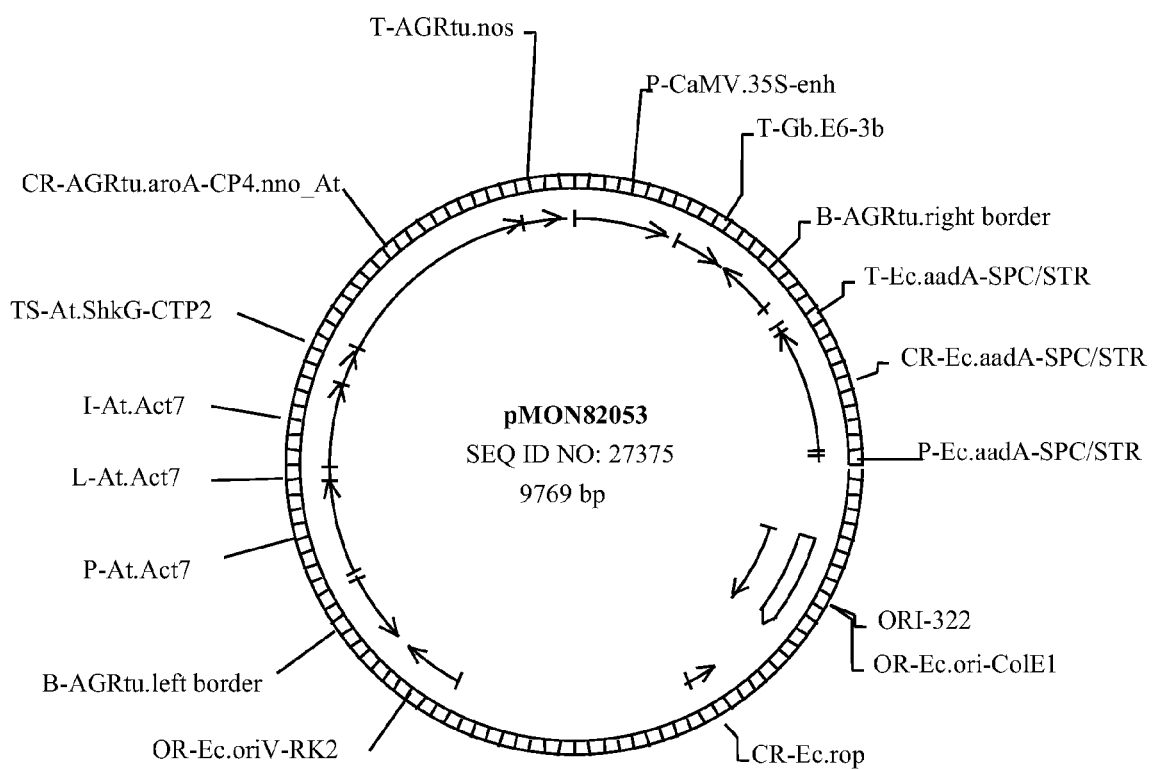

FIG. 3 Plasmid map of pMON99053
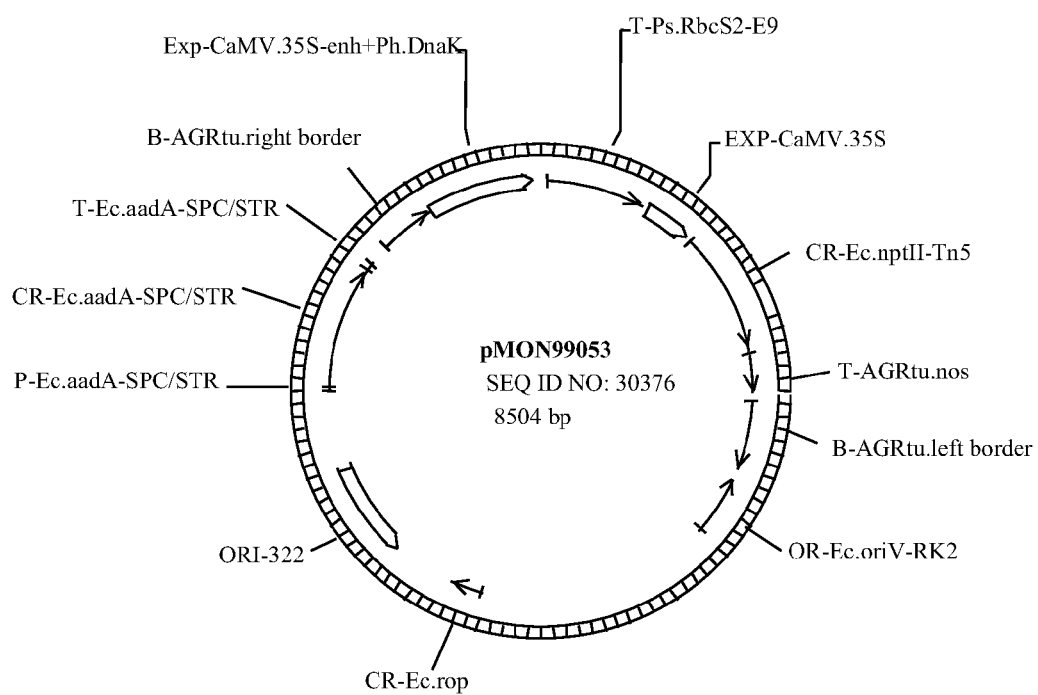

TRANSGENIC PLANTS WITH ENHANCED AGRONOMIC TRAITS

CROSS-REFERENCE TO RELATED APPLICATIONS

This application is continuation of U.S. application Ser. No. 11/982,010, filed Oct. 31, 2007, now abandoned which is a continuation-in-part of prior U.S. application Ser. No. 10/678,588 filed Oct. 2, 2003 (now abandoned), which application claims priority under 35 U.S.C. §119(e) of U.S. Provisional US Application Nos. 60/415,758, filed Oct. 2, 2002, 60/425,157, filed Nov. 8, 2002, and 60/463,787, filed Apr. 18, 2003, the disclosures of all of which are incorporated herein by reference.

This application is a continuation-in-part of prior U.S. application Ser. No. 10/310,154 filed Dec. 4, 2002 (pending), which application claims priority under 35 U.S.C. §119(e) of U.S. Provisional Application No. 60/337,358 filed Dec. 4, 2001, which applications are incorporated herein by reference in their entirety.

This application is a continuation-in-part of prior U.S. application Ser. No. 10/438,246 (pending) filed May 14, 2003, which application claims priority under 35 U.S.C. §120 as a continuation-in-part of U.S. application Ser. No. 10/155,881 filed May 22, 2002 (now abandoned); and claims priority under 35 U.S.C. §120 as a continuation-in-part of U.S. application Ser. No. 09/816,660 filed Mar. 26, 2001 (now abandoned), which is a continuation-in-part of U.S. application Ser. No. 09/733,089 filed Dec. 11, 2000 (now abandoned); and claims priority under 35 U.S.C. §120 as a continuation-in-part of U.S. application Ser. No. 09/565,306 filed May 4, 2000 (now abandoned), which claims priority under 35 U.S.C. §119(e) of U.S. Application No. 60/132,860 filed May 7, 1999; and;

claims priority under 35 U.S.C. §120 as a continuation-in-part of U.S. application Ser. No. 10/424,599 filed Apr. 28, 2003 (pending), which claims priority under 35 U.S.C. §120 as a continuation-in-part of U.S. application Ser. No. 09/985,678 filed Nov. 5, 2001 (now abandoned), which claims priority under 35 U.S.C. §120 as a continuation of Ser. No. 09/304,517 filed May 6, 1999 (now abandoned); Ser. No. 10/424,599 also claims priority under 35 U.S.C. §120 as a continuation-in-part of U.S. application Ser. No. 09/874,708, filed Jun. 5, 2001 (now abandoned), which claims priority under 35 U.S.C. §119(e) of U.S. Application No. 60/211,750, filed Jun. 15, 2000;

all of which applications are incorporated herein by reference in their entirety.

This application is a continuation-in-part of prior U.S. application Ser. No. 09/684,016 filed Oct. 10, 2000 (pending).

This application is a continuation-in-part of prior U.S. application Ser. No. 10/425,114 filed Apr. 28, 2003 (pending), which application claims priority under 35 U.S.C. §120 as a continuation-in-part of U.S. application Ser. No. 10/219,999 filed Aug. 15, 2002 (now abandoned), which application claims priority under 35 U.S.C. §119(e) of U.S. Provisional US Application Nos. 60/312,544 filed Aug. 15, 2001, and 60/324,109, filed Sep. 21, 2001, the disclosures of all of which are incorporated herein by reference.

This application is a continuation-in-part of prior U.S. application Ser. No. 11/491,125 filed Aug. 24, 2006 (pending); which application claims priority under 35 U.S.C. §119 (e) of U.S. Provisional US Application Nos. 60/144,351, filed Jul. 20, 1999; 60/163,469, filed Nov. 1, 1999; 60/177,203, filed Jan. 21, 2000; 60/184,162, filed Feb. 23, 2000; and which application is a continuation-in-part of prior U.S. application Ser. No. 09/620,392 filed Jul. 19, 2000, (now abandoned), the disclosures of all of which are incorporated herein by reference.

This application also incorporates by reference related U.S. application Ser. No. 11/982,010 filed on Oct. 31, 2007.

INCORPORATION OF SEQUENCE LISTING

Two copies of the sequence listing (Copy 1 and Copy 2) and a computer readable form (CRF) of the sequence listing, all on CD-ROMs, each containing the text file named "pa_01352.txt", which is 8.45 MB (measured in MS-WINDOWS), were created on Oct. 30, 2007 and are herein incorporated by reference.

FIELD OF THE INVENTION

Disclosed herein are inventions in the field of plant genetics and developmental biology. More specifically, the present inventions provide plant cells with recombinant DNA for providing an enhanced trait in a transgenic plant, plants comprising such cells, seed and pollen derived from such plants, methods of making and using such cells, plants, seeds and pollen.

BACKGROUND OF THE INVENTION

Transgenic plants with improved agronomic traits such as yield, environmental stress tolerance, pest resistance, herbicide tolerance, improved seed compositions, and the like are desired by both farmers and consumers. Although considerable efforts in plant breeding have provided significant gains in desired traits, the ability to introduce specific DNA into plant genomes provides further opportunities for generation of plants with improved and/or unique traits. The ability to develop transgenic plants with enhanced traits depends in part on the identification of useful recombinant DNA for production of transformed plants with enhanced properties, e.g. by actually selecting a transgenic plant from a screen for such enhanced property.

SUMMARY OF THE INVENTION

This invention provides plant cell nuclei with recombinant DNA for expression of plant HAP3 transcription factor proteins and/or 14-3-3 proteins, which proteins impart enhanced agronomic traits in transgenic plants having the nuclei in their cells, e.g. enhanced water use efficiency, enhanced cold tolerance, increased yield, enhanced nitrogen use efficiency, enhanced seed protein or enhanced seed oil. Such recombinant DNA in a plant cell nucleus of this invention is provided as a construct comprising a promoter that is functional in plant cells and that is operably linked to DNA that encodes a protein or to DNA that results in gene suppression.

Other aspects of the invention are specifically directed to transgenic plant cells comprising the recombinant DNA of the invention, transgenic plants comprising a plurality of such plant cells, progeny transgenic seed, embryo and transgenic pollen from such plants. Such transgenic plants are selected from a population of transgenic plants regenerated from plant cells transformed with recombinant DNA by screening transgenic plants in the population for an enhanced trait as compared to control plants that do not have said recombinant DNA, where the enhanced trait is selected from group of enhanced traits consisting of enhanced water use efficiency, enhanced cold tolerance, increased yield, enhanced nitrogen use efficiency, enhanced seed protein and enhanced seed oil.

In yet another aspect of the invention the plant cells, plants, seeds, embryo and pollen further comprise DNA expressing a protein that provides tolerance from exposure to an herbicide applied at levels that are lethal to a wild type plant cell. Such tolerance is especially useful not only as an advantageous trait in such plants, but is also useful in a selection step in the methods of the invention. In aspects of the invention the agent of such herbicide is a glyphosate, dicamba, or glufosinate compound.

Yet other aspects of the invention provide transgenic plants which are homozygous for the recombinant DNA and transgenic seed of the invention from corn, soybean, cotton, canola, alfalfa, sugarcane, sugar beet, wheat or rice plants.

This invention also provides methods for manufacturing non-natural, transgenic seed that can be used to produce a crop of transgenic plants with an enhanced trait resulting from expression of stably-integrated, recombinant DNA encoding plant HAP3 transcription factor proteins and/or 14-3-3 proteins in the nucleus of the plant cells. More specifically the method comprises (a) screening a population of plants for an enhanced trait and recombinant DNA, where individual plants in the population can exhibit the trait at a level less than, essentially the same as or greater than the level that the trait is exhibited in control plants which do not express the recombinant DNA; (b) selecting from the population one or more plants that exhibit the trait at a level greater than the level that said trait is exhibited in control plants and (c) collecting seed from a selected plant. Such method further comprises steps (a) verifying that the recombinant DNA is stably integrated in said selected plants; and (b) analyzing tissue of a selected plant to determine the production of HAP3 transcription factor protein or a 14-3-3 protein as provided herein. In one aspect of the invention the plants in the population further comprise DNA expressing a protein that provides tolerance to exposure to an herbicide applied at levels that are lethal to wild type plant cells and where the selecting is effected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, alfalfa, sugarcane, sugar beet, wheat or rice seed selected as having one of the enhanced traits described above.

Another aspect of the invention provides a method of producing hybrid corn seed comprising acquiring hybrid corn seed from a herbicide tolerant corn plant which also has stably-integrated, recombinant DNA comprising a promoter that is (a) functional in plant cells and (b) is operably linked to DNA that encodes a HAP3 transcription factor protein or a 14-3-3 protein as provided herein. The methods further comprise producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Another aspect of the invention provides a method of selecting a plant comprising plant cells of the invention by using an immunoreactive antibody to detect the presence of protein expressed by recombinant DNA in seed or plant tissue. Yet another aspect of the invention provides anti-counterfeit milled seed having, as an indication of origin, a plant cell of this invention.

Still other aspects of this invention relate to transgenic plants with enhanced water use efficiency or enhanced nitrogen use efficiency. For instance, this invention provides methods of growing a corn, cotton or soybean crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton or soybean crop without added nitrogen fertilizer comprising planting seed having plant cells of the invention which are selected for enhanced nitrogen use efficiency.

BRIEF DESCRIPTION OF THE DRAWINGS

FIGS. 1-3 are plasmid maps.

DETAILED DESCRIPTION OF THE INVENTION

In the attached sequence listing:

SEQ ID NO: 281, SEQ ID NO: 282, SEQ ID NO: 283, SEQ ID NO: 287, SEQ ID NO: 288, SEQ ID NO: 289, SEQ ID NO: 616, SEQ ID NO: 619, SEQ ID NO: 621, SEQ ID NO: 623, SEQ ID NO: 626, SEQ ID NO: 628, SEQ ID NO: 630, and SEQ ID NO: 632 are nucleotide sequences of the coding strand of DNA that encode plant 14-3-3 proteins.

SEQ ID NO: 1263, SEQ ID NO: 1264, SEQ ID NO: 1265, SEQ ID NO: 1269, SEQ ID NO: 1270, SEQ ID NO: 1271, SEQ ID NO: 1596, SEQ ID NO: 1599, SEQ ID NO: 1601, SEQ ID NO: 1603, SEQ ID NO: 1606, SEQ ID NO: 1608, SEQ ID NO: 1610, and SEQ ID NO: 1612 are the amino acid sequences of the plant 14-3-3 proteins.

SEQ ID NO: 783-786 are nucleotide sequences of the coding strand of DNA that encodes plant HAP3 transcription factor proteins of the present invention.

SEQ ID NO: 1763-1766 are the amino acid sequences of the plant HAP3 transcription factor proteins of the present invention.

Over expression of certain genes encoding Hap3 transcription factors having a CCAAT-box DNA binding protein impart to plants a significant resistance and/or tolerance to water deficit. See, for example, priority U.S. application Ser. No. 10/678,588 filed Oct. 2, 2003 and co-pending application U.S. Ser. No. 11/821,176, filed Jun. 23, 2007, the disclosures of which are incorporated herein by reference. The Hap3 transcription factors of this invention, which confer water deficit tolerance and/or resistance when constitutively expressed in a transgenic plant, are in a class known as CCAAT box binding DNA binding proteins. An *Arabidopsis thaliana* Hap3 transcription factor has a nucleic acid sequence of SEQ ID NO:783, and *Zea mays* Hap3 transcription factors have amino acid sequences of SEQ ID NO: 784-786. The amino acid sequence of the transcription factors of this invention, are provided as SEQ ID NOS: 1763-1766.

14-3-3 proteins have been shown to play a role in a large number of different responses in plants including regulation of plasma membrane and tonoplast ion channels, regulation of plasma membrane H(+)-ATPase activity, regulation of nitrogen metabolism including nitrate reductase activity and cytosolic glutamine synthase, regulation of carbon metabolism via modulation of sucrose phosphate synthase activities, response to nutrient starvation, import of proteins to the chloroplast and/or mitochondria and transcriptional regulation.

The structures of two 14-3-3 proteins have been determined. The proteins are dimers of C-shaped subunits that interact via a set of α-helices located in N-terminus. Dominant negative alleles of 14-3-3 proteins have been made by over expression of either C-terminal or N-terminal truncations of the protein. Over expression of N-terminal domains is thought to produce a domain that can dimerize with a wild type protein and prevent cooperative or heterologous interactions normally provided by the second subunit. This may inactivate specific 14-3-3 proteins are larger groups of the proteins as they have been shown to from heterodimers. Over expression of N-terminal truncations act by binding to phosphorylated partners and also preventing required interactions from the second subunit. However, N-terminal truncations may not be expected to inactivate other 14-3-3 family members.

14-3-3 proteins function by binding to other proteins, usually at a site centered on a phosphorylated serine residues and interaction of 14-3-3 proteins with their partner proteins is usually regulated by phosphorylation of the partner protein. Both the dependence on phosphorylation for activity and the relatively broad, constitutive expression patterns observed for most 14-3-3 genes suggest that the activity of 14-3-3 proteins may require the action of proteins other than the 14-3-3 proteins themselves.

As demonstrated herein, expression of 14-3-3 proteins in transgenic plants imparts improved agronomic traits to the transgenic plants, including tolerance to abiotic stress conditions, such as nitrogen deficiency, water stress and cold stress. Improved plant traits are obtained in transgenic plants where the expressed 14-3-3 protein is from a gene native to the transformed plant and in transgenic plants where the 14-3-3 protein is expressed from a non-native gene.

The present invention is directed to expression of 14-3-3 proteins with no truncation of either the C-terminal or N-terminal conserved domains. Such proteins will generally have an entire 14-3-3 Pfam domain (Pfam database accession ID PF00244) as defined for a 236-residue amino acid segment of conserved 14-3-3 protein sequence. A full length 14-3-3 protein generally comprises protein sequence corresponding to the entire native 14-3-3 protein, for example having from about 245 to 265 amino acids.

Transgenic plants which express both a Hap3 transcription factor and a 14-3-3 protein are of particular interest for identification of plants having improved agronomic traits.

As used herein a "plant cell" means a plant cell that is transformed with stably-integrated, non-natural, recombinant DNA, e.g. by *Agrobacterium*-mediated transformation or by baombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein "consensus sequence" means an artificial sequence of amino acids in a conserved region of an alignment of amino acid sequences of homologous proteins, e.g. as determined by a CLUSTALW alignment of amino acid sequence of homolog proteins.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. Homologous genes include naturally occurring alleles and artificially-created variants. 14-3-3 proteins belong to a highly conserved protein family, and homolog proteins useful for production of enhanced transgenic plants as described here may be identified by one skilled in the art, for example by alignment with the 14-3-3 protein sequences provided herein or by other sequence comparison methods known in the art, including by Pfam analysis. The "Pfam" database is a large collection of multiple sequence alignments and hidden Markov models covering many common protein families. The Pfam database is currently maintained and updated by the Pfam Consortium. The alignments represent some evolutionarily conserved structure that has implications for the protein's function. Profile hidden Markov models (profile HMMs) built from the protein family alignments are useful for automatically recognizing that a new protein belongs to an existing protein family even if the homology by alignment appears to be low. Thus, homologs of Hap3 transcription factors or 14-3-3 proteins may be identified from other crop plants, for example, or from other organisms, including yeast, fungi, and moss.

Degeneracy of the genetic code provides the possibility to substitute at least one base of the protein encoding sequence of a gene with a different base without causing the amino acid sequence of the polypeptide produced from the gene to be changed. Hence, a polynucleotide useful in the present invention may have any base sequence that has been changed from a HAP3 transcription factor or 14-3-3 protein coding sequence provided herein by substitution in accordance with degeneracy of the genetic code. Homologs are proteins that, when optimally aligned, have at least 60% identity, more preferably about 70% or higher, more preferably at least 80% and even more preferably at least 90% identity over the full length of a protein or domain identified herein as imparting an enhanced trait when expressed in plant cells. Homologs include proteins with an amino acid sequence that has at least 90% identity to a conserved amino acid sequence of proteins and domains disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein.

A hit is a likely ortholog, when the reciprocal query's best hit is the query protein itself or a protein encoded by a duplicated gene after speciation. A further aspect of the invention comprises functional homolog proteins that differ in one or more amino acids from those of disclosed protein as the result of conservative amino acid substitutions, for example substitutions are among: acidic (negatively charged) amino acids such as aspartic acid and glutamic acid; basic (positively charged) amino acids such as arginine, histidine, and lysine; neutral polar amino acids such as glycine, serine, threonine, cysteine, tyrosine, asparagine, and glutamine; neutral nonpolar (hydrophobic) amino acids such as alanine, leucine, isoleucine, valine, proline, phenylalanine, tryptophan, and methionine; amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine; naturally conservative amino acids such as valine-leucine, valine-isoleucine, phenylalanine-tyrosine, lysine-arginine, alanine-valine, aspartic acid-glutamic acid, and asparagine-glutamine. A further aspect of the homologs encoded by DNA useful in the transgenic plants of the invention are those proteins that differ from a disclosed protein as the result of deletion or insertion of one or more amino acids in a native sequence.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein a "control plant" means a plant that does not contain the recombinant DNA that expressed a protein that impart an enhanced trait. A control plant is to identify and select a transgenic plant that has an enhance trait. A suitable control plant can be a non-transgenic plant of the parental line used to generate a transgenic plant, i.e. devoid of recombinant DNA. A suitable control plant may in some cases be a progeny of a hemizygous transgenic plant line that is does not contain the recombinant DNA, known as a negative segregant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tonnes per acre, tons per acre, kilo per hectare. For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alterations in the ratios of seed components.

A subset of the nucleic molecules of this invention includes fragments of the disclosed recombinant DNA consisting of oligonucleotides of at least 15, preferably at least 16 or 17, more preferably at least 18 or 19, and even more preferably at least 20 or more, consecutive nucleotides. Such oligonucleotides are fragments of the larger molecules having a sequence as provided herein, and find use, for example as probes and primers for detection of the polynucleotides of the present invention.

DNA constructs are assembled using methods well known to persons of ordinary skill in the art and typically comprise a promoter operably linked to DNA, the expression of which provides the enhanced agronomic trait. Other construct components may include additional regulatory elements, such as 5' leasders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens*, caulimovirus promoters such as the cauliflower mosaic virus. For instance, see U.S. Pat. Nos. 5,858,742 and 5,322,938, which disclose versions of the constitutive promoter derived from cauliflower mosaic virus (CaMV35S), U.S. Pat. No. 5,641,876, which discloses a rice actin promoter, U.S. Patent Application Publication 2002/0192813A1, which discloses 5', 3' and intron elements useful in the design of effective plant expression vectors, U.S. patent application Ser. No. 09/757,089, which discloses a maize chloroplast aldolase promoter, U.S. patent application Ser. No. 08/706,946, which discloses a rice glutelin promoter, U.S. patent application Ser. No. 09/757,089, which discloses a maize aldolase (FDA) promoter, and U.S. Patent Application Publication No. 20030131377A1, which discloses a maize nicotianamine synthase promoter, all of which are incorporated herein by reference. These and numerous other promoters that function in plant cells are known to those skilled in the art and available for use in recombinant polynucleotides of the present invention to provide for expression of desired genes in transgenic plant cells.

In other aspects of the invention, preferential expression in plant green tissues is desired. Promoters of interest for such uses include those from genes such as *Arabidopsis thaliana* ribulose-1,5-bisphosphate carboxylase (Rubisco) small subunit (Fischhoff et al. (1992) *Plant Mol. Biol.* 20:81-93), aldolase and pyruvate orthophosphate dikinase (PPDK) (Taniguchi et al. (2000) *Plant Cell Physiol.* 41(1):42-48).

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to affect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) *Genetics* 129:863-872), glutelin 1 (Russell (1997) supra), and peroxiredoxin antioxidant (Per1) (Stacy et al. (1996) *Plant Mol. Biol.* 31(6):1205-1216).

Recombinant DNA constructs prepared in accordance with the invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, are disclosed in U.S. published patent application 2002/0192813 A1, incorporated herein by reference; the 3' element from pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. No. 5,188,642 and U.S. Pat. No. 5,728,925, incorporated herein by reference. For description of the transit peptide region of an *Arabidopsis* EPSPS gene useful in the present invention, see Klee, H. J. et al (MGG (1987) 210:437-442).

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent Application publication 2003/0083480 A1 also for imparting glyphosate tolerance; dicamba monooxygenase disclosed in U.S. Patent Application publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.*

4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for impartinig pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260, all of said U.S. Patents and Patent Application Publications are incorporated herein by reference. Molecules and methods for imparting insect/nematode/virus resistance are disclosed in U.S. Pat. Nos. 5,250,515; 5,880,275; 6,506,599; 5,986,175 and U.S. Patent Application Publication 2003/0150017 A1, all of which are incorporated herein by reference.

Plant Cell Transformation Methods

Numerous methods for transforming plant cells with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 6,384,301 (soybean), U.S. Pat. No. 7,026,528 (wheat) and U.S. Pat. No. 6,329,571 (rice), all of which are incorporated herein by reference. For *Agrobacterium tumefaciens* based plant transformation systems, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, for example, to replace an existing gene in the genome, to use an existing promoter in the plant genome, or to insert a recombinant polynucleotide at a predetermined site known to be active for gene expression. Several site specific recombination systems exist which are known to function in plants including cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, hypocotyls, calli, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, hypocotyls, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for selection of plants having an enhanced trait. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line.

In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2} s^{-1}$ of light, prior to transfer to a greenhouse or growth chamber for maturation. Plants are regenerated from about 6 weeks to 10 months after a transformant is identified, depending on the initial tissue, and the plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

water use efficiency, enhanced cold tolerance, increased yield, enhanced nitrogen use efficiency, enhanced seed protein and enhanced seed oil.

Table 1 provides a list of nucleic acid and corresponding protein sequences that are useful for production of transgenic plants with enhanced agronomic traits.

Column headings in Table 1 refer to the following information:

"NUC SEQ ID NO" refers to a particular nucleic acid sequence in the Sequence Listing which defines a polynucleotide used in a recombinant polynucleotide of this invention.

"PHE ID" refers to an arbitrary number used to identify a particular recombinant polynucleotide corresponding to the translated protein encoded by the polynucleotide.

"PEP SEQ ID NO" refers to a particular amino acid sequence in the Sequence Listing "CODING SEQUENCE" refers to peptide coding segments of the polynucleotide.

"GENE NAME" refers to a common name for the recombinant polynucleotide.

"SPECIES" refers to the organism from which the polynucleotide DNA was derived.

TABLE 1

| SEQ ID NO: | PHE ID | PEP ID NO: | Coding Sequence | Gene Name | Species |
|---|---|---|---|---|---|
| 281 | PHE0000152 | 1263 | 85-861 | 14-3-3-like protein 2 | *Glycine max* |
| 282 | PHE0000153 | 1264 | 42-824 | 14-3-3-like protein D | *Glycine max* |
| 283 | PHE0000154 | 1265 | 49-834 | 14-3-3 protein 1 | *Glycine max* |
| 287 | PHE0000158 | 1269 | 79-882 | BMH1 | *Saccharomyces cerevisiae* |
| 288 | PHE0000311 | 1270 | 81-848 | GF14-c protein | *Oryza sativa* |
| 289 | PHE0000312 | 1271 | 6-785 | 14-3-3-like protein | *Oryza sativa* |
| 616 | PHE0000854 | 1596 | 32-802 | soy 14-3-3 22 | *Glycine max* |
| 619 | PHE0000857 | 1599 | 116-874 | *sorghum* 14-3-3 10 | *Sorghum bicolor* |
| 621 | PHE0000859 | 1601 | 70-855 | rice 14-3-3 15 | *Oryza sativa* |
| 623 | PHE0000861 | 1603 | 62-808 | corn 14-3-3 13 | *Zea mays* |
| 626 | PHE0000864 | 1606 | 105-875 | rice 14-3-3 10 | *Oryza sativa* |
| 628 | PHE0000866 | 1608 | 84-860 | soy 14-3-3 21 | *Glycine max* |
| 630 | PHE0000868 | 1610 | 64-840 | wheat 14-3-3 10 | *Triticum aestivum* |
| 632 | PHE0000870 | 1612 | 132-929 | corn 14-3-3 17 | *Zea mays* |
| 783 | PHE0000002 | 1763 | 103-525 | G481 - Mendel | *Arabidopsis thaliana* |
| 784 | PHE0000003 | 1764 | 149-817 | PhenEx 67621 - corn G481-like1 | *Zea mays* |
| 785 | PHE0000004 | 1765 | 196-750 | PhenEx 67622 - corn G481-like2 | *Zea mays* |
| 786 | PHE0000005 | 1766 | 91-588 | PhenEx 67623 - corn G481-like3 | *Zea mays* |

Transgenic Plants and Seeds

Transgenic plants derived from the plant cells of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced Selection Methods for Transgenic Plants with Enhanced Agronomic Trait Within a population of transgenic plants regenerated from plant cells transformed with the recombinant DNA many plants that survive to fertile transgenic plants that produce seeds and progeny plants will not exhibit an enhanced agronomic trait. Selection from the population is necessary to identify one or more transgenic plant cells that can provide plants with the enhanced trait. Transgenic plants having enhanced traits are selected from populations of plants regenerated or derived from plant cells transformed as described herein by evaluating the plants in a variety of assays to detect an enhanced trait, e.g. enhanced water use efficiency, enhanced cold tolerance, increased yield, enhanced nitrogen use efficiency, enhanced seed protein and enhanced seed oil.

These assays also may take many forms including, but not limited to, direct screening for the trait in a greenhouse or field trial or by screening for a surrogate trait. Such analyses can be directed to detecting changes in the chemical composition, biomass, physiological properties, morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weight; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, phenotypic characteristics of harvested grain may be evaluated, including number of kernels per row on the ear, number of rows of kernels on the ear, kernel abortion, kernel weight, kernel size, kernel density and physical grain quality. Although the plant cells and methods of this invention can be applied to any plant cell, plant, seed or pollen, e.g. any fruit, vegetable, grass, tree or ornamental plant, the various aspects of the invention are preferably applied to corn, soybean, cotton, canola, alfalfa, sugarcane, sugar beet, wheat and rice plants.

The following examples are included to demonstrate aspects of the invention, those of skill in the art should, in light of the present disclosure, appreciate that many changes can be made in the specific aspects which are disclosed and still obtain a like or similar results without departing from the spirit and scope of the invention.

Example 1

Plant Expression Constructs

This example illustrates the construction of plasmid vectors for transferring recombinant DNA into plant cells which can be regenerated into transgenic plants of this invention A GATEWAY™ Destination (Invitrogen Life Technologies, Carlsbad, Calif.) plant expression vector, pMON65154, is constructed for use in preparation of constructs comprising recombinant polynucleotides for corn transformation. The elements of the expression vector are summarized in Table 2 below. Generally, pMON65154 comprises a selectable marker expression cassette comprising a Cauliflower Mosaic Virus 35S promoter operably linked to a gene encoding neomycin phosphotransferase II (nptII). The 3' region of the selectable marker expression cassette comprises the 3' region of the *Agrobacterium tumefaciens* nopaline synthase gene (nos) followed 3' by the 3' region of the potato proteinase inhibitor II (pinII) gene. The plasmid pMON 65154 further comprises a plant expression cassette into which a gene of interest may be inserted using GATEWAY™ cloning methods. The GATEWAY™ cloning cassette is flanked 5' by a rice actin 1 promoter, exon and intron and flanked 3' by the 3' region of the potato pinII gene. Using GATEWAY™ methods, the cloning cassette may be replaced with a gene of interest. The vector pMON65154, and derivatives thereof comprising a gene of interest, are particularly useful in methods of plant transformation via direct DNA delivery, such as microprojectile bombardment.

TABLE 2

Elements of Plasmid pMON65154

| FUNCTION | ELEMENT | REFERENCE |
|---|---|---|
| Plant gene of interest expression cassette | Rice actin 1 promoter | U.S. Pat. No. 5,641,876 |
| | Rice actin 1 exon 1, intron 1 enhancer | U.S. Pat. No. 5,641,876 |
| Gene of interest insertion site | AttR1 | GATEWAY ™ Cloning Technology Instruction Manual |
| | CmR gene | GATEWAY ™ Cloning Technology Instruction Manual |
| | ccdA, ccdB genes | GATEWAY ™ Cloning Technology Instruction Manual |
| | attR2 | GATEWAY ™ Cloning Technology Instruction Manual |
| Plant gene of interest expression cassette | Potato pinII 3' region | An et al. (1989) Plant Cell 1: 115-122 |
| Plant selectable marker expression cassette | CaMV 35S promoter | U.S. Pat. No. 5,858,742 |
| | nptII selectable marker | U.S. Pat. No. 5,858,742 |
| | nos 3' region | U.S. Pat. No. 5,858,742 |
| | PinII 3' region | An et al. (1989) Plant Cell 1: 115-122 |
| Maintenance in *E. coli* | ColE1 origin of replication | |
| | F1 origin of replication Bla ampicillin resistance | |

A similar plasmid vector, pMON72472, is constructed for use in *Agrobacterium* mediated methods of plant transformation. pMON72472 comprises the gene of interest plant expression cassette, GATEWAY™ cloning, and plant selectable marker expression cassettes present in pMON65154. In addition, left and right T-DNA border sequences from *Agrobacterium* are added to the plasmid (Zambryski et al. (1982) Mol Appl Genet, 1(4):361-70). The right border sequence is located 5' to the rice actin 1 promoter and the left border sequence is located 3' to the pinII 3' sequence situated 3' to the nptII gene. Furthermore, pMON72472 comprises a plasmid backbone to facilitate replication of the plasmid in both *E. coli* and *Agrobacterium tumefaciens*. The backbone has an oriV wide host range origin of DNA replication functional in *Agrobacterium*, a pBR322 origin of replication functional in *E. coli*, and a spectinomycin/streptomycin resistance gene for selection in both *E. coli* and *Agrobacterium*.

Vectors similar to those described above may be constructed for use in *Agrobacterium* or microprojectile bombardment maize transformation systems where the rice actin 1 promoter in the plant expression cassette portion is replaced with other desirable promoters including, but not limited to a corn globulin 1 promoter, a maize oleosin promoter, a glutelin 1 promoter, an RTBV promoter (U.S. Pat. No. 5,824,857), an aldolase promoter, a zein Z27 promoter, a pyruvate orthophosphate dikinase (PPDK) promoter, a a soybean 7S alpha promoter, a peroxiredoxin antioxidant (Per1) promoter and a CaMV 35S promoter. Protein coding segments are amplified by PCR prior to insertion into vectors such as described above. Primers for PCR amplification can be designed at or near the start and stop codons of the coding sequence, in order to eliminate most of the 5' and 3' untranslated regions. For GATEWAY cloning methods, PCR products are tailed with attB1 and attB2 sequences, purified then recombined into a destination vectors to produce an expression vector for use in transformation.

A. Plant Expression Constructs for Corn Transformation

A base corn transformation vector pMON93039, illustrated in Table 3 and FIG. 1, was fabricated for use in preparing recombinant DNA for *Agrobacterium*-mediated transformation into corn tissue.

TABLE 3

Elements of Plasmid pMON93039

| Function | Name | Annotation |
|---|---|---|
| *Agrobacterium* T-DNA transfer | B-AGRtu.right border | Agro right border sequence, essential for transfer of T-DNA. |
| Gene of interest expression cassette | E-Os.Act1 | Upstream promoter region of the rice actin 1 gene |
| | E-CaMV.35S.2xA1-B3 | Duplicated35S A1-B3 domain without TATA box |
| | P-Os.Act1 | Promoter region of the rice actin 1 gene |
| | L-Ta.Lhcb1 | 5' untranslated leader of wheat major chlorophyll a/b binding protein |
| | I-Os.Act1 | First intron and flanking UTR exon sequences from the rice actin 1 gene |
| | T-St.Pis4 | 3' non-translated region of the potato proteinase inhibitor II gene which functions to direct polyadenylation of the mRNA |
| Plant selectable marker expression cassette | P-Os.Act1 | Promoter from the rice actin 1 gene |
| | L-Os.Act1 | First exon of the rice actin 1 gene |
| | I-Os.Act1 | First intron and flanking UTR exon sequences from the rice actin 1 gene |
| | TS-At.ShkG-CTP2 | Transit peptide region of *Arabidopsis* EPSPS |
| | CR-AGRtu.aroA-CP4.nat | Coding region for bacterial strain CP4 native aroA gene. |
| | T-AGRtu.nos | A 3' non-translated region of the nopaline synthase gene of *Agrobacterium tumefaciens* Ti plasmid which functions to direct polyadenylation of the mRNA. |
| *Agrobacterium* T-DNA transfer | B-AGRtu.left border | Agro left border sequence, essential for transfer of T-DNA. |
| Maintenance in *E. coli* | OR-Ec.oriV-RK2 | The vegetative origin of replication from plasmid RK2. |
| | CR-Ec.rop | Coding region for repressor of primer from the ColE1 plasmid. Expression of this gene product interferes with primer binding at the origin of replication, keeping plasmid copy number low. |
| | OR-Ec.ori-ColE1 | The minimal origin of replication from the *E. coli* plasmid ColE1. |
| | P-Ec.aadA-SPC/STR | Promoter for Tn7 adenylyltransferase (AAD(3")) |
| | CR-Ec.aadA-SPC/STR | Coding region for Tn7 adenylyltransferase (AAD(3")) conferring spectinomycin and streptomycin resistance. |
| | T-Ec.aadA-SPC/STR | 3' UTR from the Tn7 adenylyltransferase (AAD(3")) gene of *E. coli*. |

B. Plant Expression Constructs for Soy and Canola Transformation

Vectors for use in transformation of soybean and canola were also prepared. Elements of an exemplary common expression vector pMON82053 are shown in Table 4 below and FIG. 2.

TABLE 4

Elements of Plasmid pMON82053

| Function | Name | Annotation |
|---|---|---|
| *Agrobacterium* T-DNA transfer | B-AGRtu.left border | Agro left border sequence, essential for transfer of T-DNA. |
| Plant selectable marker expression cassette | P-At.Act7 | Promoter from the *Arabidopsis* actin 7 gene |
| | L-At.Act7 | 5'UTR of *Arabidopsis* Act7 gene |
| | I-At.Act7 | Intron from the *Arabidopsis* actin7 gene |
| | TS-At.ShkG-CTP2 | Transit peptide region of *Arabidopsis* EPSPS |
| | CR-AGRtu.aroA- | Synthetic CP4 coding region with dicot preferred codon |

TABLE 4-continued

Elements of Plasmid pMON82053

| Function | Name | Annotation |
|---|---|---|
| | CP4.nno_At | usage. |
| | T-AGRtu.nos | A 3' non-translated region of the nopaline synthase gene of *Agrobacterium tumefaciens* Ti plasmid which functions to direct polyadenylation of the mRNA. |
| Gene of interest expression cassette | P-CaMV.35S-enh | Promoter for 35S RNA from CaMV containing a duplication of the −90 to −350 region. |
| | T-Gb.E6-3b | 3' untranslated region from the fiber protein E6 gene of sea-island cotton. |
| *Agrobacterium* T-DNA transfer | B-AGRtu.right border | Agro right border sequence, essential for transfer of T-DNA. |
| Maintenance in *E. coli* | OR-Ec.oriV-RK2 | The vegetative origin of replication from plasmid RK2. |
| | CR-Ec.rop | Coding region for repressor of primer from the ColE1 plasmid. Expression of this gene product interferes with primer binding at the origin of replication, keeping plasmid copy number low. |
| | OR-Ec.ori-ColE1 | The minimal origin of replication from the *E. coli* plasmid ColE1. |
| | P-Ec.aadA-SPC/STR | Promoter for Tn7 adenylyltransferase (AAD(3")) |
| | CR-Ec.aadA-SPC/STR | Coding region for Tn7 adenylyltransferase (AAD(3")) conferring spectinomycin and streptomycin resistance. |
| | T-Ec.aadA-SPC/STR | 3' UTR from the Tn7 adenylyltransferase (AAD(3")) gene of *E. coli*. |

Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 1 is amplified by PCR prior to insertion into the insertion site within the gene of interest expression cassette of one of the base vectors.

Vectors similar to that described above may be constructed for use in *Agrobacterium* mediated soybean transformation systems where the enhanced 35S promoter in the plant expression cassette portion is replaced with other desirable promoters including, but not limited to a napin promoter and an *Arabidopsis* SSU promoter. Protein coding segments are amplified by PCR prior to insertion into vectors such as described above. Primers for PCR amplification can be designed at or near the start and stop codons of the coding sequence, in order to eliminate most of the 5' and 3' untranslated regions.

C. Cotton Transformation Vector

Plasmids for use in transformation of cotton were also prepared. Elements of an exemplary common expression vector pMON99053 are shown in Table 5 below and FIG. 3. Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 1 is amplified by PCR prior to insertion into the insertion site within the gene of interest expression cassette of one of the base vectors.

TABLE 5

Elements of Plasmid pMON99053

| Function | Name | Annotation |
|---|---|---|
| *Agrobacterium* T-DNA transfer | B-AGRtu.right border | Agro right border sequence, essential for transfer of T-DNA. |
| Gene of interest expression cassette | Exp-CaMV.35S-enh + Ph.DnaK | Enhanced version of the 35S RNA promoter from CaMV plus the *petunia* hsp70 5' untranslated region |
| | T-Ps.RbcS2-E9 | The 3' non-translated region of the pea RbcS2 gene which functions to direct polyadenylation of the mRNA. |
| Plant selectable marker expression cassette | Exp-CaMV.35S | Promoter and 5' untranslated region from the 35S RNA of CaMV |
| | CR-Ec.nptII-Tn5 | Coding region for neomycin phosphotransferase gene from transposon Tn5 which confers resistance to neomycin and kanamycin. |
| | T-AGRtu.nos | A 3' non-translated region of the nopaline synthase gene of *Agrobacterium tumefaciens* Ti plasmid which functions to direct polyadenylation of the mRNA. |
| *Agrobacterium* T-DNA transfer | B-AGRtu.left border | Agro left border sequence, essential for transfer of T-DNA. |
| Maintenance in *E. coli* | OR-Ec.oriV-RK2 | The vegetative origin of replication from plasmid RK2. |
| | CR-Ec.rop | Coding region for repressor of primer from the ColE1 plasmid. Expression of this gene product interferes with primer binding at the origin of replication, keeping plasmid copy number low. |
| | OR-Ec.ori-ColE1 | The minimal origin of replication from the *E. coli* plasmid ColE1. |

TABLE 5-continued

Elements of Plasmid pMON99053

| Function | Name | Annotation |
|---|---|---|
| | P-Ec.aadA-SPC/STR | Promoter for Tn7 adenylyltransferase (AAD(3")) |
| | CR-Ec.aadA-SPC/STR | Coding region for Tn7 adenylyltransferase (AAD(3")) conferring spectinomycin and streptomycin resistance. |
| | T-Ec.aadA-SPC/STR | 3' UTR from the Tn7 adenylyltransferase (AAD(3")) gene of E. coli. |

An alternative plant selectable marker expression cassette that finds use in generation and selection of transgenic cotton plants comprises a chimeric FMV-EF1alpha promoter, such as described in WO01/44457, regulating expression of a CP4 gene that confers tolerance to glyphosate herbicide.

Example 2

Corn Transformation

This example illustrates plant cell transformation methods useful in producing transgenic corn plant cells, plants, seeds and pollen of this invention and the production and identification of transgenic corn plants and seed with an enhanced trait, i.e. enhanced water use efficiency, enhanced cold tolerance, increased yield, enhanced nitrogen use efficiency, enhanced seed protein and enhanced seed oil. Plasmid vectors were prepared by cloning DNA identified in Table 1 in the identified base vectors for use in corn transformation of corn plant cells to produce transgenic corn plants and progeny plants, seed and pollen.

For *Agrobacterium*-mediated transformation of corn embryo cells corn plants of a readily transformable line (designated LH59) are grown in the greenhouse and ears are harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, *Agrobacterium* cells are grown overnight at room temperature. Immature maize embryo cells are inoculated with *Agrobacterium* shortly after excision, and incubated at room temperature with *Agrobacterium* for 5-20 minutes. Immature embryo plant cells are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformed plant cells are recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

For transformation by microprojectile bombardment maize immature embryos are isolated and cultured 3-4 days prior to bombardment. Prior to microprojectile bombardment, a suspension of gold particles is prepared onto which the desired recombinant DNA expression cassettes are precipitated. DNA is introduced into maize cells as described in U.S. Pat. Nos. 5,550,318 and 6,399,861 using the electric discharge particle acceleration gene delivery device. Following microprojectile bombardment, tissue is cultured in the dark at 27° C. Additional transformation methods and materials for making transgenic plants of this invention, for example, various media and recipient target cells, transformation of immature embryos and subsequence regeneration of fertile transgenic plants are disclosed in U.S. Pat. Nos. 6,194,636 and 6,232,526 and U.S. patent application Ser. No. 09/757,089, which are incorporated herein by reference.

To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

Transgenic corn plant cells are transformed with recombinant DNA from each of the genes identified in Table 1. Progeny transgenic plants and seed of the transformed plant cells are screened for enhanced water use efficiency, enhanced cold tolerance, increased yield, enhanced nitrogen use efficiency, enhanced seed protein and enhanced seed oil as reported in Example 6.

Example 3

Soybean Transformation

This example illustrates plant transformation useful in producing the transgenic soybean plants of this invention and the production and identification of transgenic seed for transgenic soybean having enhanced water use efficiency, enhanced cold tolerance, increased yield, enhanced nitrogen use efficiency, enhanced seed protein and enhanced seed oil.

For *Agrobacterium* mediated transformation, soybean seeds are imbided overnight and the meristem explants excised. The explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed imbibition, and wounded using sonication. Following wounding, explants are placed in co-culture for 2-5 days at which point they are transferred to selection media for 6-8 weeks to allow selection and growth of transgenic shoots. Resistant shoots are harvested approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil. Additionally, a DNA construct can be transferred into the genome of a soybean cell by particle bombardment and the cell regenerated into a fertile soybean plant as described in U.S. Pat. No. 5,015,580, herein incorporated by reference.

Transgenic soybean plant cells are transformed with recombinant DNA from each of the genes identified in Table 1. Transgenic progeny plants and seed of the transformed plant cells are screened for enhanced water use efficiency, enhanced cold tolerance, increased yield, enhanced nitrogen use efficiency, enhanced seed protein and enhanced seed oil as reported in Example 6.

Example 4

Cotton Transgenic Plants with Enhanced Agronomic Traits

Cotton transformation is performed as generally described in WO0036911 and in U.S. Pat. No. 5,846,797. Transgenic cotton plants containing each of the recombinant DNA having a sequence as described herein are obtained by transforming with recombinant DNA from each of the genes identified in Table 1. Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, i.e. cotton variety ST474, cotton variety FM 958, and cotton variety Siokra L-23, are used to compare the relative performance of the transgenic cotton plants containing the recombinant DNA. The specified culture conditions are growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, i.e. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates, and improved fiber parameters.

The transgenic cotton plants of this invention are identified from among the transgenic cotton plants by agronomic trait screening as having increased yield and enhanced water use efficiency.

Example 5

Canola Transformation

This example illustrates plant transformation useful in producing the transgenic canola plants of this invention and the production and identification of transgenic seed for transgenic canola having enhanced water use efficiency, enhanced cold tolerance, increased yield, enhanced nitrogen use efficiency, enhanced seed protein and enhanced seed oil.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterization are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant Transgenic canola plant cells are transformed with recombinant DNA from each of the genes identified in Table 1. Transgenic progeny plants and seed of the transformed plant cells are screened for enhanced water use efficiency, enhanced cold tolerance, increased yield, enhanced nitrogen use efficiency, enhanced seed protein and enhanced seed oil as reported in Example 6.

Example 6

Selection of Transgenic Plants with Enhanced Agronomic Trait(s)

This example illustrates identification of plant cells of the invention by screening derived plants and seeds for enhanced trait. Transgenic corn seed and plants with recombinant DNA identified in Table 1 are prepared by plant cells transformed with DNA that is stably integrated into the genome of the corn cell. Transgenic corn plant cells are transformed with recombinant DNA from the genes identified in Table 1. The promoter for expression of the genes is a rice actin promoter, as described in Table 2, unless otherwise specified herein. Progeny transgenic plants and seed of the transformed plant cells are screened for enhanced water use efficiency, enhanced cold tolerance, increased yield, enhanced nitrogen use efficiency, enhanced seed protein and enhanced seed oil as compared to control plants.

A. Selection for Enhanced Nitrogen Use Efficiency

The physiological efficacy of transgenic corn plants (tested as hybrids) can be tested for nitrogen use efficiency (NUE) traits in a high-throughput nitrogen (N) selection method. The collected data are compared to the measurements from wildtype controls using a statistical model to determine if the changes are due to the transgene. Raw data were analyzed by SAS software. Results shown herein are the comparison of transgenic plants relative to the wildtype controls.

(1) Media Preparation for Planting a NUE Protocol

Planting materials used: Metro Mix 200 (vendor: Hummert) Cat. #10-0325, Scotts Micro Max Nutrients (vendor:

Hummert) Cat. #07-6330, OS 4⅓"×3⅞" pots (vendor: Hummert) Cat. #16-1415, OS trays (vendor: Hummert) Cat. #16-1515, Hoagland's macronutrients solution, Plastic 5" stakes (vendor: Hummert) yellow Cat. #49-1569, white Cat. #49-1505, Labels with numbers indicating material contained in pots. Fill 500 pots to rim with Metro Mix 200 to a weight of ~140 g/pot. Pots are filled uniformly by using a balancer. Add 0.4 g of Micro Max nutrients to each pot. Stir ingredients with spatula to a depth of 3 inches while preventing material loss.

(2) Planting a NUE Selection in the Greenhouse (a) Seed Germination—Each pot is lightly watered twice using reverse osmosis purified water. The first watering is scheduled to occur just before planting; and the second watering, after the seed has been planted in the pot. Ten Seeds of each entry (1 seed per pot) are planted to select eight healthy uniform seedlings. Additional wild type controls are planted for use as border rows. Alternatively, 15 seeds of each entry (1 seed per pot) are planted to select 12 healthy uniform seedlings (this larger number of plantings is used for the second, or confirmation, planting). Place pots on each of the 12 shelves in the Conviron growth chamber for seven days. This is done to allow more uniform germination and early seedling growth. The following growth chamber settings are 25° C./day and 22° C./night, 14 hours light and ten hours dark, humidity ~80%, and light intensity ~350 μmol/m²/s (at pot level). Watering is done via capillary matting similar to greenhouse benches with duration of ten minutes three times a day.

(b) Seedling transfer—After seven days, the best eight or 12 seedlings for the first or confirmation pass runs, respectively, are chosen and transferred to greenhouse benches. The pots are spaced eight inches apart (center to center) and are positioned on the benches using the spacing patterns printed on the capillary matting. The Vattex matting creates a 384-position grid, randomizing all range, row combinations. Additional pots of controls are placed along the outside of the experimental block to reduce border effects.

Plants are allowed to grow for 28 days under the low N run or for 23 days under the high N run. The macronutrients are dispensed in the form of a macronutrient solution (see composition below) containing precise amounts of N added (2 mM $NH_4NO_3$ for limiting N selection and 20 mM $NH_4NO_3$ for high N selection runs). Each pot is manually dispensed 100 ml of nutrient solution three times a week on alternate days starting at eight and ten days after planting for high N and low N runs, respectively. On the day of nutrient application, two 20 min waterings at 05:00 and 13:00 are skipped. The vattex matting should be changed every third run to avoid N accumulation and buildup of root matter. Table 6 shows the amount of nutrients in the nutrient solution for either the low or high nitrogen selection.

TABLE 6

| Nutrient Stock | 2 mM $NH_4NO_3$ (Low Nitrogen Growth Condition, Low N) mL/L | 20 mM $NH_4NO_3$ (High Nitrogen Growth Condition, High N) mL/L |
|---|---|---|
| 1M $NH_4NO_3$ | 2 | 20 |
| 1M $KH_2PO_4$ | 0.5 | 0.5 |
| 1M $MgSO_4 \cdot 7H_2O$ | 2 | 2 |
| 1M $CaCl_2$ | 2.5 | 2.5 |
| 1M $K_2SO_4$ | 1 | 1 |

Note:
Adjust pH to 5.6 with HCl or KOH (c) Harvest Measurements and Data Collection—After 28 days of plant growth for low N runs and 23 days of plant growth for high N runs, the following measurements are taken (phenocodes in parentheses): total shoot fresh mass (g) (SFM) measured by Sartorius electronic balance, V6 leaf chlorophyll measured by Minolta SPAD meter (relative units) (LC), V6 leaf area (cm²) (LA) measured by a Li-Cor leaf area meter, V6 leaf fresh mass (g) (LFM) measured by Sartorius electronic balance, and V6 leaf dry mass (g) (LDM) measured by Sartorius electronic balance. Raw data were analyzed by SAS software. Results shown are the comparison of transgenic plants relative to the wildtype controls.

To take a leaf reading, samples were excised from the V6 leaf. Since chlorophyll meter readings of corn leaves are affected by the part of the leaf and the position of the leaf on the plant that is sampled, SPAD meter readings were done on leaf six of the plants. Three measurements per leaf were taken, of which the first reading was taken from a point one-half the distance between the leaf tip and the collar and halfway from the leaf margin to the midrib while two were taken toward the leaf tip. The measurements were restricted in the area from ½ to ¾ of the total length of the leaf (from the base) with approximately equal spacing between them. The average of the three measurements was taken from the SPAD machine.

Leaf fresh mass is recorded for an excised V6 leaf, the leaf is placed into a paper bag. The paper bags containing the leaves are then placed into a forced air oven at 80° C. for 3 days. After 3 days, the paper bags are removed from the oven and the leaf dry mass measurements are taken.

From the collected data, two derived measurements are made: (1) Leaf chlorophyll area (LCA), which is a product of V6 relative chlorophyll content and its leaf area (relative units). Leaf chlorophyll area=leaf chlorophyll X leaf area. This parameter gives an indication of the spread of chlorophyll over the entire leaf area; (2) specific leaf area (LSA) is calculated as the ratio of V6 leaf area to its dry mass (cm²/g dry mass), a parameter also recognized as a measure of NUE.

A list of recombinant DNA constructs which improved growth in high nitrogen in transgenic corn plants is illustrated in Table 7.

TABLE 7

| NUC SEQ ID | PEP SEQ ID | PHE ID | Construct | Positive events/ Total events screened | Confirmed events/ Actual events with confirmation attempted |
|---|---|---|---|---|---|
| 785 | 1765 | PHE0000004 | PMON67819 | 2/2 | 2/2 |
| 786 | 1766 | PHE0000005 | PMON67820 | 2/2 | 2/2 |
| 616 | 1596 | PHE0000854 | PMON73795 | 1/1 | 0/0 |

A list of recombinant DNA constructs which improved growth in limited nitrogen in transgenic corn plants is illustrated in Table 8.

TABLE 8

| NUC SEQ ID | PEP SEQ ID | PHE ID | Construct | Positive events/ Total events screened | Confirmed events/ Actual events with confirmation attempted |
|---|---|---|---|---|---|
| 783 | 1763 | PHE0000002 | PMON80861 | 3/4 | 2/4 |
| 785 | 1765 | PHE0000004 | PMON67819 | 2/3 | 0/3 |
| 786 | 1766 | PHE0000005 | PMON67820 | 3/7 | 0/4 |
| 616 | 1596 | PHE0000854 | PMON73795 | 1/3 | 1/1 |
| 619 | 1599 | PHE0000857 | PMON75348 | 2/5 | 2/5 |
| 621 | 1601 | PHE0000859 | PMON73798 | 1/8 | 0/0 |
| 628 | 1608 | PHE0000866 | PMON84970 | 2/10 | 0/0 |

B. Selection for Increased Yield

Many transgenic plants of this invention exhibit improved yield as compared to a control plant. Improved yield can result from enhanced seed sink potential, i.e. the number and size of endosperm cells or kernels and/or enhanced sink strength, i.e. the rate of starch biosynthesis. Sink potential can be established very early during kernel development, as endosperm cell number and size are determined within the first few days after pollination.

Much of the increase in corn yield of the past several decades has resulted from an increase in planting density. During that period, corn yield has been increasing at a rate of 2.1 bushels/acre/year, but the planting density has increased at a rate of 250 plants/acre/year. A characteristic of modern hybrid corn is the ability of these varieties to be planted at high density. Many studies have shown that a higher than current planting density should result in more biomass production, but current germplasm does not perform. well at these higher densities. One approach to increasing yield is to increase harvest index (HI), the proportion of biomass that is allocated to the kernel compared to total biomass, in high density plantings.

It is to plant multiple transgenic plants, positive and negative control plants, and pollinator plants in standard plots, for example 2 row plots, 20 feet long by 5 feet wide with 30 inches distance between rows and a 3 foot alley between ranges. Transgenic events can be grouped by recombinant DNA constructs with groups randomly placed in the field. A pollinator plot of a high quality corn line is planted for every two plots to allow open pollination when using male sterile transgenic events. A useful planting density is about 30,000 plants/acre. High planting density is greater than 30,000 plants/acre, preferably about 40,000 plants/acre, more preferably about 42,000 plants/acre, most preferably about 45,000 plants/acre. Surrogate indicators for yield improvement include source capacity (biomass), source output (sucrose and photosynthesis), sink components (kernel size, ear size, starch in the seed), development (light response, height, density tolerance), maturity, early flowering trait and physiological responses to high density planting, for example at 45,000 plants per acre, for example as illustrated in Tables 9 and 10.

TABLE 9

| Timing | Evaluation | Description | Comments |
|---|---|---|---|
| V2-3 | Early stand | Can be taken any time after germination and prior to removal of any plants. | |
| Pollen shed | GDU to 50% shed | GDU to 50% plants shedding 50% tassel. | |
| Silking | GDU to 50% silk | GDU to 50% plants showing silks. | |
| Maturity | Plant height | Height from soil surface to flag leaf attachment (inches). | 10 plants per plot |
| Maturity | Ear height | Height from soil surface to primary ear attachment node. | 10 plants per plot |
| Maturity | Leaves above ear | visual scores: erect, size, rolling | |
| Maturity | Tassel size | Visual scores +/− vs. WT | |
| Pre-Harvest | Final stand | Final stand count prior to harvest, exclude tillers | |
| Pre-Harvest | Stalk lodging | No. of stalks broken below the primary ear attachment. Exclude leaning tillers | |
| Pre-Harvest | Root lodging | No. of stalks leaning >45° angle from perpendicular. | |
| Pre-Harvest | Stay green | After physiological maturity and when differences among genotypes are evident: Scale 1 (90-100% tissue green)-9 (0-19% tissue green). | |
| Harvest | Grain yield | Grain yield/plot (Shell weight) | |

Effective yield selection of enhanced yielding transgenic corn events uses hybrid progeny of the transgenic event over multiple locations with plants grown under optimal production management practices, and maximum pest control. A useful target for improved yield is a 5% to 10% increase in yield as compared to yield produced by plants grown from seed for a control plant. Selection methods may be applied in multiple and diverse geographic locations, for example up to 16 or more locations, over one or more plating seasons, for example at least two planting seasons to statistically distinguish yield improvement from natural environmental effects.

TABLE 10

| Timing | Evaluation | Description |
|---|---|---|
| V8-V12 | Chlorophyll | |
| V12-VT | Ear leaf area | |
| V15-15 DAP | Chl fluorescence | |
| V15-15 DAP | CER | |

TABLE 10-continued

| Timing | Evaluation | Description |
|---|---|---|
| 15-25 DAP | Carbohydrates | sucrose, starch |
| Pre-Harvest | 1st internode diameter | |
| Pre-Harvest | Base 3 internode diameter | |
| Pre-Harvest | Ear internode diameter | |
| Maturity | Ear traits | diameter, length, kernel number, kernel weight |

Electron transport rates (ETR) and CO2 exchange rates (CER): ETR and CER are measured with Li6400LCF (Licor, Lincoln, Nebr.) around V9-R1 stages. Leaf chlorophyll fluorescence is a quick way to monitor the source activity and is reported to be highly correlated with $CO_2$ assimilation under varies conditions (Photosyn Research, 37: 89-102). The youngest fully expanded leaf or 2 leaves above the ear leaf is measured with actinic light 1500 (with 10% blue light) micromol $M^{-2}$ $s^{-1}$, 28° C., $CO_2$ levels 450 ppm. Ten plants are measured in each event. There are 2 readings for each plant.

A hand-held chlorophyll meter SPAD-502 (Minolta—Japan) is used to measure the total chlorophyll level on live transgenic plants and the wild type counterparts. Three trifoliates from each plant are analyzed, and each trifoliate was analyzed three times. The 9 data points are averaged to obtain the chlorophyll level. The number of analyzed plants of each genotype ranges from 5 to 8.

When selecting for yield improvement a useful statistical measurement approach comprises three components, i.e. modeling spatial autocorrelation of the test field separately for each location, adjusting traits of recombinant DNA events for spatial dependence for each location, and conducting an across location analysis. The first step in modeling spatial autocorrelation is estimating the covariance parameters of the semivariogram. A spherical covariance model is assumed to model the spatial autocorrelation. Because of the size and nature of the trial, it is likely that the spatial autocorrelation may change. Therefore, anisotropy is also assumed along with spherical covariance structure. The following set of equations describes the statistical form of the anisotropic spherical covariance model.

$$C(h; \theta) = vI(h=0) + \sigma^2\left(1 - \frac{3}{2}h + \frac{1}{2}h^3\right)I(h<1),$$

where I(●) is the indicator function, $h=\sqrt{\dot{x}^2+\dot{y}^2}$, and $\dot{x}=[\cos(\rho\pi/180)(x_1-x_2)-\sin(\rho\pi/180)(y_1-y_2)]/\omega_x$ $\dot{y}=[\sin(\rho\pi/180)(x_1-x_2)+\cos(\rho\pi/180)(y_1-y_2)]/\omega_y$ where $s_1=(x_1, y_1)$ are the spatial coordinates of one location and $s_2=(x_2, y_2)$ are the spatial coordinates of the second location. There are 5 covariance parameters, $\theta=(v, \sigma^2, \rho, \omega_n, \omega_j)$, where $v$ is the nugget effect, $\sigma^2$ is the partial sill, $\rho$ is a rotation in degrees clockwise from north, $\omega_n$ is a scaling parameter for the minor axis and $\omega_j$ is a scaling parameter for the major axis of an anisotropical ellipse of equal covariance. The five covariance parameters that defines the spatial trend will then be estimated by using data from heavily replicated pollinator plots via restricted maximum likelihood approach. In a multi-location field trial, spatial trend are modeled separately for each location.

After obtaining the variance parameters of the model, a variance-covariance structure is generated for the data set to be analyzed. This variance-covariance structure contains spatial information required to adjust yield data for spatial dependence. In this case, a nested model that best represents the treatment and experimental design of the study is used along with the variance-covariance structure to adjust the yield data. During this process the nursery or the seed batch effects can also be modeled and estimated to adjust the yields for any yield parity caused by seed batch differences. After spatially adjusted data from different locations are generated, all adjusted data is combined and analyzed assuming locations as replications. In this analysis, intra and inter-location variances are combined to estimate the standard error of yield from transgenic plants and control plants. Relative mean comparisons are used to indicate statistically significant yield improvements.

A list of recombinant DNA constructs which show improved yield in transgenic corn plants is illustrated in Table 11.

TABLE 11

| NUC SEQ ID | PEP SEQ ID | PHE ID | Construct | Positive events/ Total events screened | Confirmed events/ Actual events with confirmation attempted |
|---|---|---|---|---|---|
| 785 | 1765 | PHE0000004 | PMON67819 | 1/7 | 0/3 |
| 786 | 1766 | PHE0000005 | PMON67820 | 1/11 | 0/6 |
| 786 | 1766 | PHE0000005 | PMON73601 | 1/2 | 0/1 |
| 632 | 1612 | PHE0000870 | PMON75340 | 1/1 | 0/1 |

C. Selection for Enhanced Water Use Efficiency (WUE)

(1) Greenhouse and Growth Chamber Screens for Enhanced Water Use Efficiency

Described in this example is a high-throughput method for greenhouse selection of transgenic corn plants to wild type corn plants (tested as inbreds or hybrids) for water use efficiency. This selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment. The hydration status of the shoot tissues following the drought is also measured. Plant height is measured at three time points. The first is taken just prior to the onset drought when the plant is 11 days old, which is the shoot initial height (SIH). Plant height is also measured halfway throughout the drought/re-water regimen, on day 18 after planting, to give rise to the shoot mid-drought height (SMH). Upon completion of the final drought cycle on day 26 after planting, the shoot portion of the plant is harvested and measured for a final height, which is the shoot wilt height (SWH), and also measured for shoot wilted biomass (SWM). The shoot is placed in water at 40 degree Celsius in the dark. Three days later, the shoot is weighed to give rise to the shoot turgid weight (STM). After drying in an oven for four days, the shoots are weighed for shoot dry biomass (SDM). The shoot average height (SAH) is the mean plant height across the 3 height measurements. The procedure described above may be adjusted for +/−one day for each step given the situation.

To correct for slight differences between plants, a size corrected growth value is derived from SIH and SWH. This is the Relative Growth Rate (RGR). Relative Growth Rate (RGR) is calculated for each shoot using the formula [RGR %=(SWH−SIH)/((SWH+SIH)/2)*100]. Relative water content (RWC) is a measurement of how much (%) of the plant was water at harvest. Water Content (RWC) is calculated for each shoot using the formula [RWC %=(SWM−SDM)/(STM−SDM)*100]. Fully watered corn plants of this age run around 98% RWC.

A list of recombinant DNA constructs which improved water use efficiency in transgenic corn plants is illustrated in Table 12.

green leaves, reduced tassel emergence, little or no silk emergence, little or poor ear development. The duration of this low water regime typically is timed to span the V8 leaf through the R2 reproductive stage.

To identify individual plants that show improved growth under stress conditions, at least two persons walk through the field at various times between the VT and R2 stages of plant development to allow for both identification and verification of drought tolerance. Plants that represent 1-2% of the population that best exhibits improved cumulative vegetative and reproductive characteristics, e.g. greenness, plant height/internode expansion, leaf flatness/wilting, ear development, silk development/vigor and tassel development/emergence are identified. Identified plants are tagged with an ID, photographed, and sampled for further analysis.

Leaf samples are taken from individual plants showing a positive growth response under water stress. Because the quality of the plant material is important for quality of molecular analysis, the youngest/freshest leaf material is col-

TABLE 12

| NUC SEQ ID | PEP SEQ ID | PHE ID | Construct | Positive events/ Total events screened | Confirmed events/ Actual events with confirmation attempted |
|---|---|---|---|---|---|
| 785 | 1765 | PHE0000004 | PMON67819 | 3/7 | 2/4 |
| 785 | 1765 | PHE0000004 | PMON82452 | 6/11 | 0/0 |
| 786 | 1766 | PHE0000005 | PMON67820 | 4/11 | 2/11 |
| 616 | 1596 | PHE0000854 | PMON73795 | 1/4 | 0/2 |
| 619 | 1599 | PHE0000857 | PMON75348 | 2/6 | 0/4 |

Transgenic soy plants expressing Hap3 transcription factor proteins of SEQ ID NO: 1763 and SEQ ID NO: 1765 are tested in a growth chamber seedling wilt assay and demonstrated to have improved tolerance to water deficit conditions.

(2) Screening Large Field Populations for Enhanced Water Use Efficiency

The following description illustrates the selection of transgenic corn hybrid plants having improved water use efficiency from large field populations of, for example, over 13,000 hybrid corn plants representing hundreds to thousands of transgenic events prepared by transformation methods. Hybrid corn seeds for each of the transgenic events are randomized in a tumbler to create a pool of seeds. Multiple sets of an identical pool may be prepared for planting at different locations.

Seeds of identical pools are planted at multiple test locations at a density of approximately 32,000 plants/acre. Plants are evenly spaced in the field to ensure that environmental effects are similar for each plant in the field. The plot structure can be, for example, conventional corn rows on 30″ centers. Each row is planted with drip-tape to facilitate uniform water distribution of water to initiate germination. To generate water stress or drought conditions, the population stand is allowed to attain V8 stage of growth under normal watering conditions. At V8 stage, irrigation water is withheld until about 98% of the population exhibits extreme drought symptoms, e.g. very rolled leaves, poor internode expansion, light lected for analysis. DNA is isolated from the tissue samples and used as template for amplification of the inserted transgenic DNA using commercially available sequencing kits. The resulting sequence information is compared to the known set of transgene coding region sequences used in the field study.

The null hypothesis is that the selection of plants is no better than selecting plants randomly. Chi square analysis is used to test the null hypothesis for each plant construct in the study. Since it is known how many plants for a given construct were planted in the field and how many plants were selected and sampled, the expected frequency of randomly selecting a transgenic plant that contains a given construct can be calculated. Sequence identification of the sampled plants allows for calculation of the observed frequency for a given construct in the sampled population. Chi square analysis indicates if the observed frequency for a construct is significantly different from random. If the frequency of identifying a particular construct is significantly higher than random (at $P \leq 0.05$), it indicates that the null hypothesis (the selection of plants is no better than selecting plants randomly) is not true. This demonstrates that the gene in plants where the null hypothesis is not true has improved plant growth under stress conditions. A list of recombinant DNA constructs which improved water use efficiency in transgenic corn plants as demonstrated by field testing as described above is illustrated in Table 13.

TABLE 13

| PEP SEQ ID | Construct | ID | Gene Name | Events | Exp. Freq. | Obs. Freq. | Chi Test |
|---|---|---|---|---|---|---|---|
| 1596 | pMON73795 | PHE0000854 | Soy 14-3-3 22 | 3 | 0.87 | 3 | 0.023 |
| 1265 | pMON85035 | PHE0000154 | 14-3-3 protein 1 | 10 | 1.86 | 5 | .021 |

TABLE 13-continued

| PEP SEQ ID | Construct | ID | Gene Name | Events | Exp. Freq. | Obs. Freq. | Chi Test |
|---|---|---|---|---|---|---|---|
| 1264 | pMON96114 | PHE0000153 | 14-3-3-like protein D | 8 | 1.4 | 7 | 0.0000 |
| 1608 | pMON84970 | PHE0000866 | soy 14-3-3 21 | 6 | 1.12 | 4 | .006 |
| 1610 | PMON75338 | PHE0000868 | wheat 14-3-3 10 | 4 | 1.22 | 4 | .012 |

(3) Greenhouse and Field Level Analysis of Transgenic Cotton Plants

Transgenic cotton plants transformed with pMON95503 and expressing soy 14-3-3 22 protein (PHE0000854) under the regulatory control of a CaMV 35S promoter are analyzed for enhanced agronomic traits in greenhouse and field tests. In greenhouse tests, transgenic plants are identified which have an increase in plant height, number of nodes and internode length, as well as increased number of squares and bolls. When the events were tested against water use efficiency it was also noted that several of the events had an increase in plant fresh mass and plant dry mass (calculated based on total biomass/amount of water given). Field level analysis of pMON95503 transgenic plants confirms that the plants have enhanced agronomic traits, including increased vigor and increased numbers of bolls and nodes under water stress conditions.

Transgenic cotton plants expressing the plant Hap3 transcription factor protein of SEQ ID NO: 1763 under the regulatory control of a CaMV 35S promoter (pMON83103) demonstrate improved properties when grown under well watered and water stress conditions in the field. Positive events showed a lower rate of soil moisture depletion and greater growth rate under sustained deficit irrigation conditions. Hap3 transcription factor protein expressing plants were taller than control plants under both well watered and sustained deficit irrigation conditions. When plant height was normalized relative to the initial size at the onset of differential irrigation, Hap3 transcription factor protein expressing plants under well-watered conditions were significantly taller than the corresponding negative isoline controls. Differences in plant height are due to differences in internode length (equal node number). Transgenic plants expressing the plant Hap3 transcription factor protein of SEQ ID NO: 1763 under the regulatory control of an rd29a promoter (pMON95538) or a Tsf1 promoter (pMON95539) are similarly analyzed to identify transgenic cotton plants with improved agronomic traits.

D. Selection for Growth Under Cold Stress

Cold germination assay—Three sets of seeds are used for the assay. The first set consists of positive transgenic events (F1 hybrid) where the genes of the present invention are expressed in the seed. The second seed set is nontransgenic, wild-type negative control made from the same genotype as the transgenic events. The third set consisted of two cold tolerant and one cold sensitive commercial check lines of corn. All seeds are treated with a fungicide "Captan" (MAESTRO® 80DF Fungicide, Arvesta Corporation, San Francisco, Calif., USA). 0.43 mL Captan is applied per 45 g of corn seeds by mixing it well and drying the fungicide prior to the experiment.

Corn kernels are placed embryo side down on blotter paper within an individual cell (8.9×8.9 cm) of a germination tray (54×36 cm). Ten seeds from an event are placed into one cell of the germination tray. Each tray can hold 21 transgenic events and 3 replicates of wildtype (LH244SDms+LH59), which is randomized in a complete block design. For every event there are five replications (five trays). The trays are placed at 9.7° C. for 24 days (no light) in a Conviron growth chamber (Conviron Model PGV36, Controlled Environments, Winnipeg, Canada). Two hundred and fifty millilters of deionized water are added to each germination tray. Germination counts are taken 10th, 11th, 12th, 13th, 14th, 17th, 19th, 21st, and 24th day after start date of the experiment. Seeds are considered germinated if the emerged radicle size is 1 cm. From the germination counts germination index is calculated.

The germination index is calculated as per:

$$\text{Germination index} = (\Sigma([T+1-n_i]*[P_i-P_{i-1}]))/T$$

Where T is the total number of days for which the germination assay is performed. The number of days after planting is defined by n. "i" indicates the number of times the germination has been counted, including the current day. P is the percentage of seeds germinated during any given rating. Statistical differences are calculated between transgenic events and wild type control. After statistical analysis, the events that show a statistical significance at a p-level of less than 0.1 relative to wild-type controls will advance to a secondary cold selection. The secondary cold screen is conducted in the same manner of the primary selection only increasing the number of repetitions to ten. Statistical analysis of the data from the secondary selection is conducted to identify the events that show a statistical significance at a p-level of less than 0.05 relative to wild-type controls.

A list of recombinant DNA constructs which improve growth in seed under cold stress in transgenic corn plants is illustrated in Table 14.

TABLE 14

| NUC SEQ ID | PEP SEQ ID | PHE ID | Construct | Positive events/ Total events screened | Confirmed events/ Actual events with confirmation attempted |
|---|---|---|---|---|---|
| 785 | 1765 | PHE0000004 | PMON67819 | 1/5 | 1/1 |
| 786 | 1766 | PHE0000005 | PMON67820 | 7/11 | 3/9 |
| 628 | 1608 | PHE0000866 | PMON84970 | 1/7 | 0/0 |

E. Screens for Transgenic Plant Seeds with Increased Protein and/or Oil Levels

This example sets forth a high-throughput selection for identifying plant seeds with improvement in seed composition using the Infratec 1200 series Grain Analyzer, which is a near-infrared transmittance spectrometer used to determine the composition of a bulk seed sample (Table 10). Near infrared analysis is a non-destructive, high-throughput method that can analyze multiple traits in a single sample scan. An NIR calibration for the analytes of interest is used to predict the values of an unknown sample. The NIR spectrum is obtained for the sample and compared to the calibration using a complex chemometric software package that provides a predicted values as well as information on how well the sample fits in the calibration.

Infratec Model 1221, 1225, or 1227 with transport module by Foss North America is used with cuvette, item #1000-4033, Foss North America or for small samples with small cell cuvette, Foss standard cuvette modified by Leon Girard Co. Corn and soy check samples of varying composition maintained in check cell cuvettes are supplied by Leon Girard Co. NIT collection software is provided by Maximum Consulting Inc. Software. Calculations are performed automatically by the software. Seed samples are received in packets or containers with barcode labels from the customer. The seed is poured into the cuvettes and analyzed as received. The detail information has been provided in Table 15.

TABLE 15

| | |
|---|---|
| Typical sample(s): | Whole grain corn and soybean seeds |
| Analytical time to run method: | Less than 0.75 min per sample |
| Total elapsed time per run: | 1.5 minute per sample |
| Typical and minimum sample size: | Corn typical: 50 cc; minimum 30 cc |
| | Soybean typical: 50 cc; minimum 5 cc |
| Typical analytical range: | Determined in part by the specific calibration. |
| | Corn - moisture 5-15%, oil 5-20%, protein 5-30%, starch 50-75%, and density 1.0-1.3%. |
| | Soybean - moisture 5-15%, oil 15-25%, and protein 35-50%. |

A list of recombinant DNA constructs which improve seed compositions in terms of protein content in transgenic corn plants is illustrated in Table 16.

TABLE 16

| NUC SEQ ID | PEP SEQ ID | PHE ID | Construct | Positive events/ Total events screened | Confirmed events/ Actual events with confirmation attempted |
|---|---|---|---|---|---|
| 785 | 1765 | PHE0000004 | PMON67819 | 1/7 | 0/0 |
| 786 | 1766 | PHE0000005 | PMON67820 | 1/8 | 0/0 |
| 619 | 1599 | PHE0000857 | PMON75348 | 5/6 | 0/2 |
| 621 | 1601 | PHE0000859 | PMON73798 | 5/8 | 5/5 |
| 630 | 1610 | PHE0000868 | PMON75338 | 1/4 | 0/0 |
| 632 | 1612 | PHE0000870 | PMON75340 | 1/1 | 0/2 |

A list of recombinant DNA constructs which improve seed compositions in terms of oil content in transgenic corn plants is illustrated in Table 17.

TABLE 17

| NUC SEQ ID | PEP SEQ ID | PHE ID | Construct | Positive events/ Total events screened | Confirmed events/ Actual events with confirmation attempted |
|---|---|---|---|---|---|
| 785 | 1765 | PHE0000004 | PMON67819 | 1/3 | 0/0 |
| 786 | 1766 | PHE0000005 | PMON67820 | 1/6 | 0/0 |

Example 7

Transgenic Plants with Enhanced Agronomic Traits from Expression of HAP3 Transcription Factor and 14-3-3 Proteins This example illustrates the preparation and identification by selection of transgenic seeds and plants where the plants and seeds are modified for expression of both HAP3 transcription factor and 14-3-3 proteins. Transgenic plants are generated by transformation with recombinant DNA constructs which provide for expression of at least one HAP3 transcription factor protein and at least one 14-3-3 protein, such as disclosed herein. Alternatively, transgenic plants are generated by crossing HAP3 transcription factor expressing plants as provided herein with 14-3-3 protein expressing plants as provided herein.

Transgenic plant cells of corn, soybean, cotton, canola, alfalfa, sugarcane, sugar beet, wheat and rice expressing both HAP3 transcription factor and 14-3-3 proteins and having enhanced agronomic traits are screened as described in Example 6 for enhanced water use efficiency, enhanced cold tolerance, increased yield, enhanced nitrogen use efficiency, enhanced seed protein and enhanced seed oil. Plants are identified exhibiting enhanced traits imparted by expression of the HAP3 transcription factor and 14-3-3 proteins.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09322031B2). An electronic copy of the "Sequence Listing" will also be available from the USPTO upon request and payment of the fee set forth in 37 CFR 1.19(b)(3).

What is claimed is:

1. A method of producing a plant having enhanced tolerance to water deficit stress comprising:
   (i) introducing a recombinant DNA into one or more plants to obtain one or more transgenic plant lines, wherein said recombinant DNA comprises a heterologous promoter functional in a plant cell operably linked to a polynucleotide encoding a plant HAP3 transcription factor protein comprising an amino acid sequence with at least 90% identity over the full length of the SEQ ID NO: 1765 amino acid sequence;
   (ii) screening for said enhanced tolerance to water deficit stress in a trial wherein said transgenic plant lines are exposed to water deficit stress; and,
   (iii) selecting from the screened transgenic plant line(s) of (ii) a transgenic plant or progeny thereof that exhibits enhanced tolerance to water deficit stress, wherein said tolerance to water deficit stress is enhanced in comparison to a control plant that does not have said recombinant DNA and wherein expression of said plant HAP3 transcription factor protein imparts said enhanced trait; and wherein said selected transgenic plant or progeny thereof comprise said recombinant DNA.

2. The method of claim 1, wherein said plant HAP3 transcription factor protein comprises the amino acid sequence of SEQ ID NO: 1765.

3. The method of claim 1, wherein said plant is corn, soybean, cotton, alfalfa, sugarcane, sugar beet, wheat or rice plant.

4. A method of growing a corn, cotton or soybean crop without irrigation water comprising:
   (i) planting seed that give rise to plants selected for enhanced water use efficiency, wherein the genome of said seed and said selected plants comprises a recombinant DNA that comprises a heterologous promoter functional in a plant cell that is operably linked to a polynucleotide encoding a plant HAP3 transcription factor protein comprising an amino acid sequence with at least 90% identity over the full length of the SEQ ID NO: 1765 amino acid sequence and wherein expression of said HAP3 protein imparts to said selected plants enhanced water use efficiency in comparison to control plants that do not have said recombinant DNA; and,
   (ii) growing 0 said selected plants obtained from said seed without irrigation water to obtain said crop, and wherein said seed or selected plants are from corn, cotton or soybean.

5. A method of growing a corn or cotton crop with reduced irrigation water comprising:
   (i) planting seed that give rise to plants selected for enhanced water use efficiency, wherein the genome of said seed and said selected plants comprises a recombinant DNA that comprises a heterologous promoter functional in a plant cell that is operably linked to a polynucleotide encoding a plant HAP3 transcription factor protein comprising an amino acid sequence with at least 90% identity over the full length of the SEQ ID NO: 1765 amino acid sequence and wherein expression of said HAP3 protein imparts to said selected plants enhanced water use efficiency trait in comparison to control plants that do not have said recombinant DNA, and wherein said seed or selected plants are from corn or cotton;
   and,
   (ii) growing said selected plants obtained from said seed with reduced irrigation by providing up to 300 millimeters of ground water during production of said corn crop, or by irrigating in the range of 40 to 60 percent of evapotranspiration to provide a leaf water potential of −21 to −25 bars during production of said cotton crop.

6. The method of claim 4, wherein said plant HAP3 transcription factor protein comprises the amino acid sequence of SEQ ID NO: 1765.

7. The method of claim 4, wherein said recombinant DNA further comprises a linked herbicide tolerance marker.

8. The method of claim 5, wherein said plant HAP3 transcription factor protein comprises the amino acid sequence of SEQ ID NO: 1765.

9. The method of claim 5, wherein said recombinant DNA further comprises a linked herbicide tolerance marker.

* * * * *